United States Patent
Miller

(10) Patent No.: US 8,426,428 B2
(45) Date of Patent: Apr. 23, 2013

(54) EGFR KINASE KNOCKDOWN VIA ELECTROPHILICALLY ENHANCED INHIBITORS

(75) Inventor: Richard Miller, Portola Valley, CA (US)

(73) Assignee: Principia Biopharma, Inc., South San Francisco, CA (US)

( * ) Notice: Subject to any disclaimer, the term of this patent is extended or adjusted under 35 U.S.C. 154(b) by 676 days.

(21) Appl. No.: 12/329,445

(22) Filed: Dec. 5, 2008

(65) Prior Publication Data

US 2010/0144705 A1    Jun. 10, 2010

(51) Int. Cl.
*C07D 487/04* (2006.01)
*A61K 31/519* (2006.01)
*A61P 35/00* (2006.01)
*A61P 29/00* (2006.01)

(52) U.S. Cl.
USPC ...... 514/262.1; 544/262; 544/280; 514/265.1

(58) Field of Classification Search .................. 544/262; 514/262.1
See application file for complete search history.

(56) References Cited

U.S. PATENT DOCUMENTS

| | | | |
|---|---|---|---|
| 5,763,596 A | 6/1998 | Boyer et al. | |
| 5,763,597 A | 6/1998 | Ugarkar et al. | |
| 5,795,977 A | 8/1998 | Ugarkar et al. | |
| 6,921,763 B2 * | 7/2005 | Hirst et al. | 514/262.1 |
| 2003/0153752 A1 | 8/2003 | Hirst et al. | |
| 2008/0076921 A1 | 3/2008 | Honigberg et al. | |

FOREIGN PATENT DOCUMENTS

| | | |
|---|---|---|
| WO | WO-97-32879 A1 | 9/1997 |
| WO | WO-97-34895 A1 | 9/1997 |
| WO | WO-2010-065898 A2 | 6/2010 |
| WO | WO-2010-065898 A3 | 6/2010 |

OTHER PUBLICATIONS

Apsel et. al. (Nature Chemical Biology, 2008, 4(11), pp. 691-699 and supplemental material, p. 163).*
Kwak et al., "Irreversible inhibitors of the EGF receptor may circumvent acquired resistance to gefitinib," Proc Natl Acad Sci USA 102(21):7665-7670 (2005).
PCT/US09/66831 Search Report dated Aug. 25, 2010.

* cited by examiner

*Primary Examiner* — Susanna Moore
(74) *Attorney, Agent, or Firm* — Finnegan, Henderson, Farabow, Garrett & Dunner, LLP

(57) ABSTRACT

Provided herein are electrophilically enhanced kinase inhibitors of Formula I. Also provided herein are methods of making and utilizing the same.

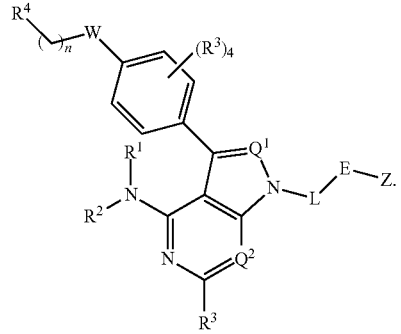

Formula I

13 Claims, 3 Drawing Sheets

EGFR KINASE KNOCKDOWN VIA ELECTROPHILICALLY ENHANCED INHIBITORS

BACKGROUND OF THE INVENTION

Figure 1:
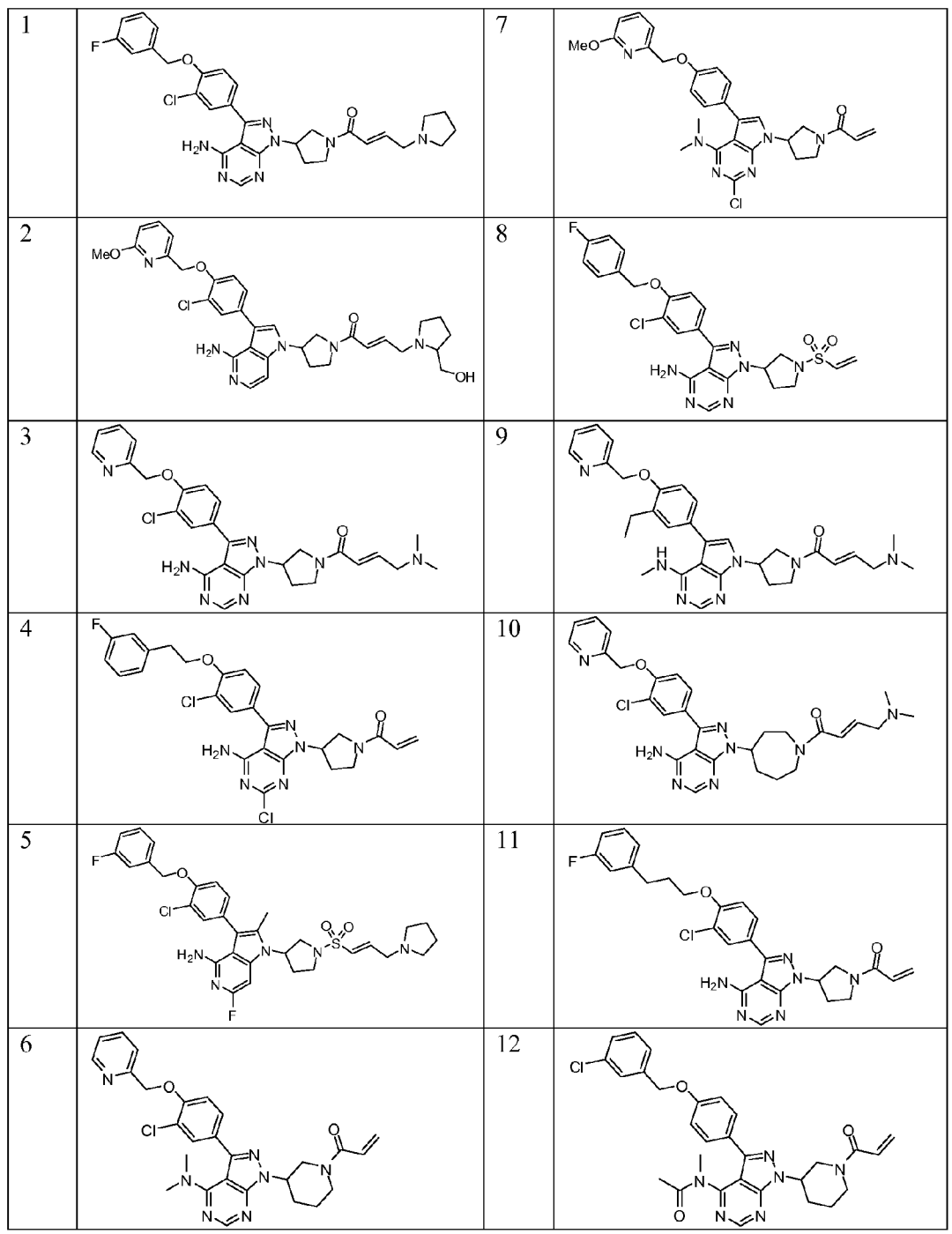

Kinases play critical roles in signaling pathways controlling fundamental cellular processes such as proliferation, differentiation, and death (apoptosis).

SUMMARY OF THE INVENTION

Described herein are kinase inhibitors that bind irreversibly to kinases that contain a nucleophilic amino acid residue near the ATP-binding site of the kinase. Such kinase inhibitors include an electrophilic moiety that reacts with the nucleophilic amino acid residue to form a covalent bond. Further such kinase inhibitors include a moiety that binds non-covalently to the ATP-binding site of the kinase. In other words, such kinase inhibitors include a non-covalent ATP-binding site moiety and an electrophilic moiety that react with a nucleophilic amino acid residue to form a covalent bond. In certain embodiments, the nucleophilic amino acid residue is a cysteine residue. In certain embodiments, the effect of such kinase inhibitors is to knockdown such kinases so that such a kinase is no longer reactive with at least one native substrate or ligand.

In some embodiments, such kinase inhibitors reversibly bind to kinases that do not contain a nucleophilic amino acid residue near the ATP-binding site of such a kinase, but irreversibly bind to kinases that do have a nucleophilic amino acid residue near the ATP-binding site.

Also described herein is the use of such kinase inhibitors for the treatment of diseases or conditions in which the activity of a kinase having a nucleophilic amino acid reside near its ATP-binding site contributes to the etiology or the symptoms of such a disease or condition. Administration of such kinase inhibitors irreversibly inhibits (or knockdown) the activity of such a kinase and provides therapeutic benefit to an individual afflicted with such a disease or condition.

Also described herein are kinase inhibitors that irreversibly inhibit kinases that have a nucleophilic amino acid residue near its ATP-binding site and which are reversibly inhibited by e.g. N-(3—CHloro-4-{[(3-fluorophenyl)methyl]oxy}phenyl)-6-[5-({[2-(methylsulfonyl)ethyl]amino}methyl)-2-furanyl]-4-quinazolinamine ("Compound 100"). In certain embodiments, the compounds described herein (i.e., compounds of Formula I) are used to treat a patient that has a disease or condition that is either refractory to Compound 100, insufficiently responsive to Compound 100, or in which Compound 100 produces unacceptable toxicity, side effects or adverse events (including those resulting from the promiscuity of Compound 100 with other kinases). Such diseases or conditions are described herein. In certain embodiments, the compounds described herein (i.e., compounds of Formula I) are used to treat a disease or condition in a patient who is also prescribed Compound 100.

In certain embodiments are kinase inhibitors that reversibly inhibit kinases that do not have a nucleophilic amino acid residue near its ATP-binding site.

In certain of any of the aforementioned embodiments, the nucleophilic amino acid residue is a cysteine and the kinase is a tyrosine kinase.

Provided in certain embodiments herein are compounds of Formula I:

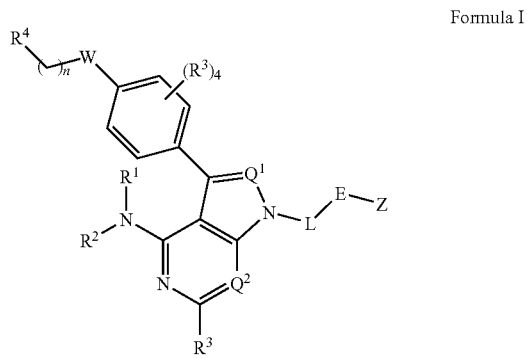

Formula I wherein:
each $R^1$ and $R^2$ is H, substituted or unsubstituted alkyl, substituted or unsubstituted heteroalkyl, $C(=O)R^5$ or $C(=NR^5)$; wherein $R^5$ is H, hydroxy, substituted or unsubstituted alkyl or substituted or unsubstituted alkoxy;

each $R^3$ is independently H, halo, hydroxy, CN, substituted or unsubstituted alkyl, substituted or unsubstituted alkoxy, or substituted or unsubstituted heteroalkyl;

each $R^4$ is independently substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

W is $—CH_2—$, $—C\equiv C—$, O, S, or $NR^1$;

n is 1-7

$Q^1$ is N or $CR^3$;

$Q^2$ is N or $CR^3$;

L is $A_p$, wherein
each A is independently $NR^1$, $S(O)_q$, O, $C(=X)Y$, $Y(C=X)$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;

p is 0-5;

E is an electrophile;

Z is $—(Z^1)_k—Z^2$ or is absent,
$Z^1$ is $NR^6$, O, $C(=X)Y$, $Y(C=X)$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl $Z^2$ is H, $NR^6_2$, $S(O)_qR^6$, $OR^6$, $—C(=X)YR^6$, $—Y(C=X)R^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

each $R^6$ is independently H, halo, hydroxy, alkoxy, cyano, nitro, $—C(=X)YR^7$, $—YC(=X)R^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein $R^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;

k is 0-4;

each X is independently S or O;

each Y is independently S or O;

or a pharmaceutically acceptable salt thereof.

In certain embodiments, E is an electrophile subject to nucleophilic substitution or nucleophilic addition when contacted with a thiol and/or a thiolate.

In specific embodiments, provided herein are compounds of Formula I,
wherein E is:

—(CR$^{14}$R$^{15}$)$_r$—(CR$^8$═CR$^8$)$_q$—(CR$^{14}$R$^{15}$)$_r$— wherein

R$^{14}$ and R$^{15}$ are independently H, CN, NO$_2$, substituted or unsubstituted alkyl, substituted or unsubstituted aryl, or substituted or unsubstituted heteroaryl, or taken together are ═S, ═N—OR$^{11}$, or ═O; wherein each R$^{11}$ is independently substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;

each R$^8$ is independently H, halo, hydroxy, alkoxy, cyano, nitro, S(O)$_{1-2}$R$^{11}$, —C(═X)YR$^{11}$, —YC(═X)R$^{11}$, substituted or unsubstituted alkyl, substituted or unsubstituted aryl, substituted or unsubstituted cycloalkyl, substituted or unsubstituted heteroaryl, substituted or unsubstituted heterocycloalkyl, substituted or unsubstituted heteroalkyl, or two R$^8$ are taken together to form a bond;

each r is independently 0-2;

q is 0-2;

—(CR$^9$R$^{10}$)—X$^2$ wherein

R$^9$ and R$^{10}$ are independently H, halo, hydroxy, alkoxy, cyano, nitro, —C(═X)YR$^{11}$, —YC(═X)R$^{11}$, substituted or unsubstituted alkyl, substituted or unsubstituted aryl, substituted or unsubstituted cycloalkyl, substituted or unsubstituted heteroaryl, substituted or unsubstituted heterocycloalkyl, substituted or unsubstituted heteroalkyl, or is a bond to Z; or R$^9$ and R$^{10}$ taken together are ═O or ═S;

X$^2$ is halo, OR$^{12}$, NR$^{12}$$_v$, N$_3$, SR$^{12}$, or SCN; wherein R$^{12}$ is —(S(O)$_t$)$_u$—R$^{13}$; wherein each R$^{13}$ is independently H, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl; or X$^2$ and R$^{10}$ when taken together with the carbon to which they are bound form an oxirane or oxetane; wherein t is 1-2, wherein u is 0-1, wherein v is 2-3;

—NR$^{11}$(C═O)O—; —O(C═O)NR$^{11}$—; —CR$^{11}$R$^{16}$(C═O)—; or —CR$^{11}$R$^{16}$(C═O)—, wherein R$^{16}$ is halo.

In certain embodiments, R$^1$ and R$^2$ are independently H or substituted or unsubstituted alkyl. In some embodiments, Q$^1$ is N. In some embodiments, Q$^1$ is CH. In some embodiments, Q$^2$ is N. In some embodiments, Q$^2$ is CH. In some embodiments, R$^3$ is H, halo, substituted or unsubstituted alkyl, or substituted or unsubstituted alkoxy. In some embodiments, W is —CH$_2$— or O. In some embodiments, n is 1-3.

In some specific embodiments, E is —(C═O)—(CH═CH)—, —(CH═CH)—(C═O)—, —C(CN)═CH—, —CH═C(CN)—, —C(NO$_2$)═CH—, —CH═C(NO$_2$)—, —(SO$_2$)—(CH═CH)—, or —(CH═CH)—(SO$_2$)—.

In some embodiments, n is 1 or 2, and one A is tetrahydroquinolinyl, quinolinyl, tetrahydroisoquinolinyl, isoquinolinyl, phenyl, cyclohexyl, cyclopentyl, pyridinyl, pyrimidinyl, piperidinyl, homopiperidinyl, pyrrolidinyl, piperazinyl or morpholino. In some embodiments, n is 1 or 2, and one A is phenyl, cyclohexyl, cyclopentyl, pyridinyl, pyrimidinyl, piperidinyl, homopiperidinyl, pyrrolidinyl, piperazinyl or morpholino.

In certain specific embodiments, Z$^2$ is NR$^6$$_2$, substituted or unsubstituted heteroalkyl, substituted or unsubstituted piperidinyl, substituted or unsubstituted pyrrolidinyl, substituted or unsubstituted piperazinyl or a substituted or unsubstituted morpholino.

In some embodiments, provided herein are compounds of Formula Ia:

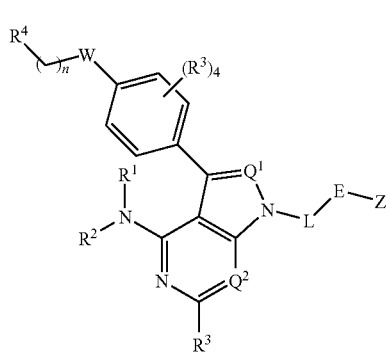

Formula Ia wherein:
Q$^1$ is N or CH;
Q$^2$ is N or CH;

In some specific embodiments, provided herein are compounds of Formula I having the Formula II:

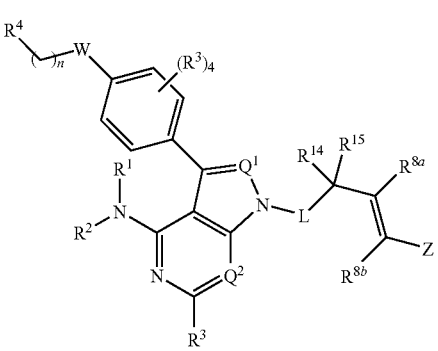

Formula II wherein
R$^3$ is H, halo, substituted or unsubstituted alkyl or substituted or unsubstituted alkoxy;
R$^4$ is substituted or unsubstituted aryl, substituted or unsubstituted heteroaryl, substituted or unsubstituted cycloalkyl, or substituted or unsubstituted heterocycloalkyl;

$R^{14}$ is H;
$R^{15}$ is H; or $R^{14}$ and $R^{15}$ taken together are =O;
$R^{8a}$ is H, lower alkyl, CN, $NO_2$, or $SO_2R^{11}$; and
$R^{8b}$ is H, CN, $NO_2$, or $SO_2R^{11}$.

In certain specific embodiments, $R^4$ is substituted or unsubstituted aryl, or substituted or unsubstituted heteroaryl. In some embodiments, $R^3$ is H, Cl or F. In some embodiments, $R^{14}$ and $R^{15}$ taken together are =O, and wherein $R^{8a}$ and $R^{8b}$ are H. In some specific embodiments, $Q^1$ is N and $Q^2$ is N. In some embodiments, W is O. In certain embodiments, $R^1$ is H and $R^2$ is H. In some embodiments, n is 1. In certain specific embodiments, $R^4$ is substituted or unsubstituted pyridinyl.

In certain embodiments, a compound of Formula I is selective for one or more ErbB kinase.

Also provided in certain embodiments herein is a pharmaceutical composition comprising a therapeutically effective amount of a compound of Formula I:

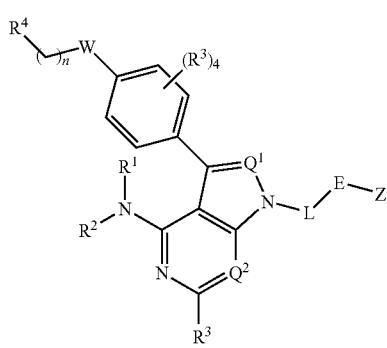

Formula I wherein:
each $R^1$
and $R^2$ is H, substituted or unsubstituted alkyl, substituted or unsubstituted heteroalkyl, C(=O)$R^5$ or C(=N$R^5$);
wherein $R^5$ is H, hydroxy, substituted or unsubstituted alkyl or substituted or unsubstituted alkoxy;
each $R^3$ is independently H, halo, hydroxy, CN, substituted or unsubstituted alkyl, substituted or unsubstituted alkoxy, or substituted or unsubstituted heteroalkyl;
each $R^4$ is independently substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
W is —$CH_2$—, —C=C—, O, S, or $NR^1$;
n is 1-7
$Q^1$ is N or $CR^3$;
$Q^2$ is N or $CR^3$;
L is $A_p$, wherein
each A is independently $NR^1$, S(O)$_q$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;
p is 0-5;
E is an electrophile;
Z is —$(Z^1)_k$—$Z^2$ or is absent,
$Z^1$ is $NR^6$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl
$Z^2$ is H, $NR^6_2$, S(O)$_q R^6$, $OR^6$, —C(=X)Y$R^6$, —Y(C=X)$R^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
each $R^6$ is independently H, halo, hydroxy, alkoxy, cyano, nitro, —C(=X)Y$R^7$, —YC(=X)$R^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein $R^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;
k is 0-4;
each X is independently S or O;
each Y is independently S or O;
or a pharmaceutically acceptable salt thereof;
and a pharmaceutically acceptable carrier.

Provided in some embodiments herein is a method of treating a disorder mediated by a cysteine containing kinase comprising administering to an individual in need thereof a therapeutically effective amount of a compound of Formula I:

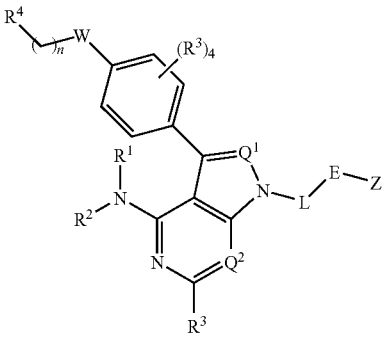

Formula I wherein:
each $R^1$
and $R^2$ is H, substituted or unsubstituted alkyl, substituted or unsubstituted heteroalkyl, C(=O)$R^5$ or C(=N$R^5$);
wherein $R^5$ is H, hydroxy, substituted or unsubstituted alkyl or substituted or unsubstituted alkoxy;
each $R^3$ is independently H, halo, hydroxy, CN, substituted or unsubstituted alkyl, substituted or unsubstituted alkoxy, or substituted or unsubstituted heteroalkyl;
each $R^4$ is independently substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
W is —$CH_2$—, —C=C—, O, S, or $NR^1$;
n is 1-7
$Q^1$ is N or $CR^3$;
$Q^2$ is N or $CR^3$;

L is $A_p$, wherein
  each A is independently $NR^1$, $S(O)_q$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;
  p is 0-5;
E is an electrophile;
Z is —$(Z^1)_k$—$Z^2$ or is absent,
  $Z^1$ is $NR^6$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl
  $Z^2$ is H, $NR^6_2$, $S(O)_qR^6$, $OR^6$, —C(=X)$YR^6$, —Y(C=X)$R^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
  each $R^6$ is independently H, halo, hydroxy, alkoxy, cyano, nitro, —C(=X)$YR^7$, —YC(=X)$R^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein $R^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;
  k is 0-4;
  each X is independently S or O;
  each Y is independently S or O;
  or a pharmaceutically acceptable salt thereof.

In specific embodiments, the cysteine containing kinase comprises a cysteine in proximity to the ATP binding site of the kinase. In some embodiments, the cysteine containing kinase is BMX, TEC, TXK, ITK, EGFR, ErbB2, ErbB4, JAK3, or BLK. In some embodiments, the cysteine containing kinase is EGFR, ErbB2, or ErbB4. In certain embodiments, the disorder is cancer, an inflammatory disorder, or an autoimmune disorder mediated by the cysteine containing kinase.

Provided in some embodiments herein is a method of binding a cysteine containing kinase to a compound of Formula I comprising contacting the kinase with the compound of Formula I, wherein the compound of Formula I has the structure:

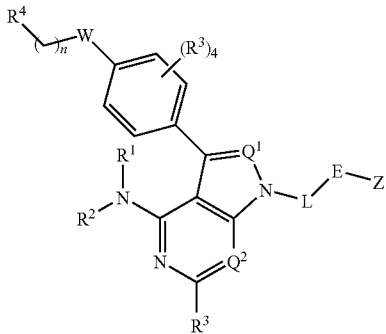

Formula I wherein:
  each $R^1$ and $R^2$ is H, substituted or unsubstituted alkyl, substituted or unsubstituted heteroalkyl, C(=O)$R^5$ or C(=$NR^5$); wherein $R^5$ is H, hydroxy, substituted or unsubstituted alkyl or substituted or unsubstituted alkoxy;
  each $R^3$ is independently H, halo, hydroxy, CN, substituted or unsubstituted alkyl, substituted or unsubstituted alkoxy, or substituted or unsubstituted heteroalkyl;
  each $R^4$ is independently substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
  W is —$CH_2$—, —C=C—, O, S, or $NR^1$;
  n is 1-7
  $Q^1$ is N or $CR^3$;
  $Q^2$ is N or $CR^3$;
  L is $A_p$, wherein
    each A is independently $NR^1$, $S(O)_q$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;
    p is 0-5;
  E is an electrophile;
  Z is —$(Z^1)_k$—$Z^2$ or is absent,
    $Z^1$ is $NR^6$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl
    $Z^2$ is H, $NR^6_2$, $S(O)_qR^6$, $OR^6$, —C(=X)$YR^6$, —Y(C=X)$R^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
    each $R^6$ is independently H, halo, hydroxy, alkoxy, cyano, nitro, —C(=X)$YR^7$, —YC(=X)$R^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein $R^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;
    k is 0-4;
    each X is independently S or O;
    each Y is independently S or O;
  or a pharmaceutically acceptable salt thereof.

In specific embodiments, the cysteine containing kinase is BMX, TEC, TXK, ITK, EGFR, ErbB2, ErbB4, JAK3, or BLK. In certain embodiments, the method of binding a cysteine containing kinase is a method of selectively binding EGFR, ErbB2, ErbB4, or a combination thereof. In certain embodiments, the kinase is contacted with the compound of Formula I in vivo.

DETAILED DESCRIPTION OF THE FIGURES

FIG. 1 presents illustrative examples of compounds described herein.

Figure 2:
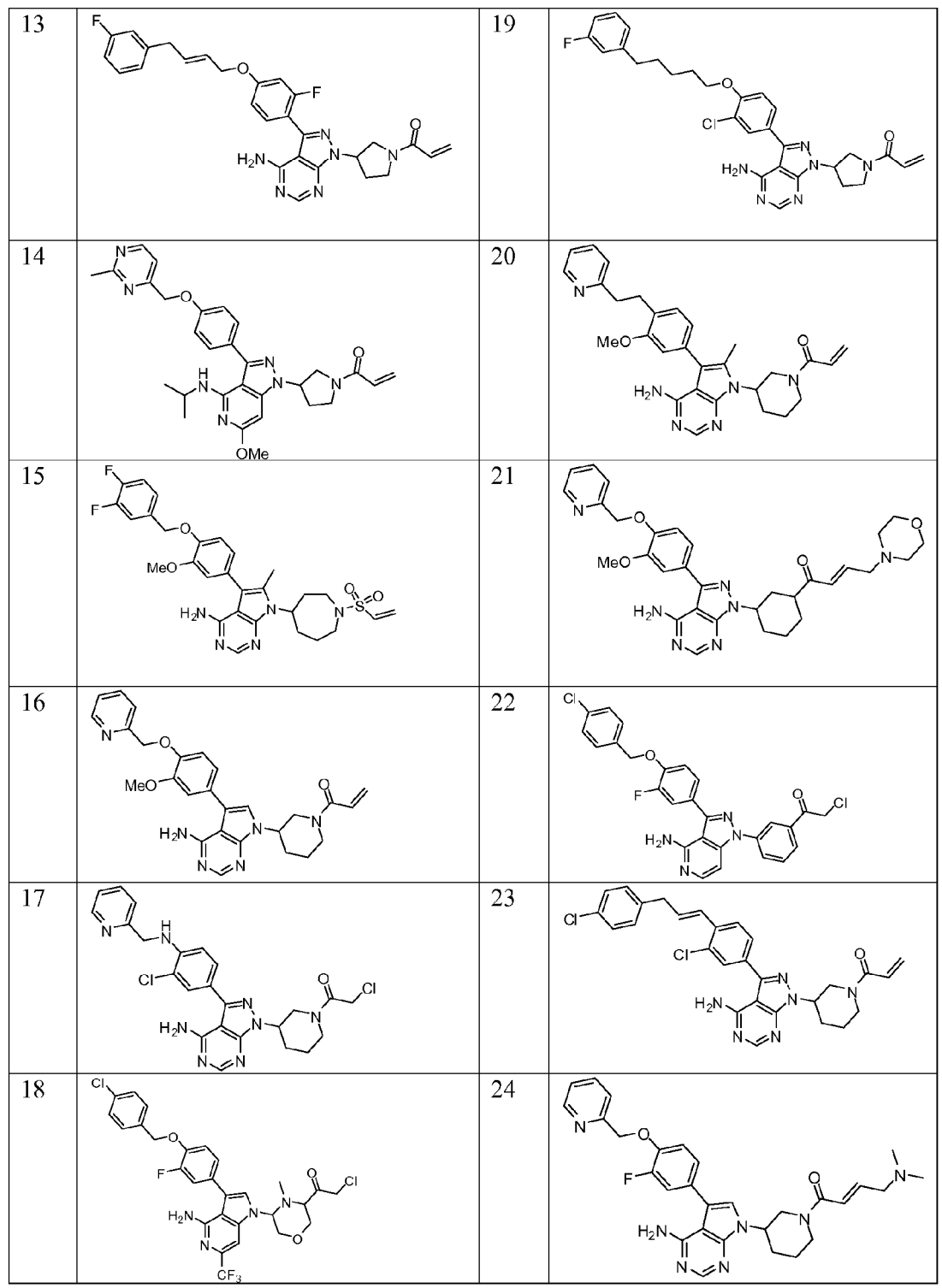

FIG. 2 presents illustrative examples of compounds described herein.

Figure 3:
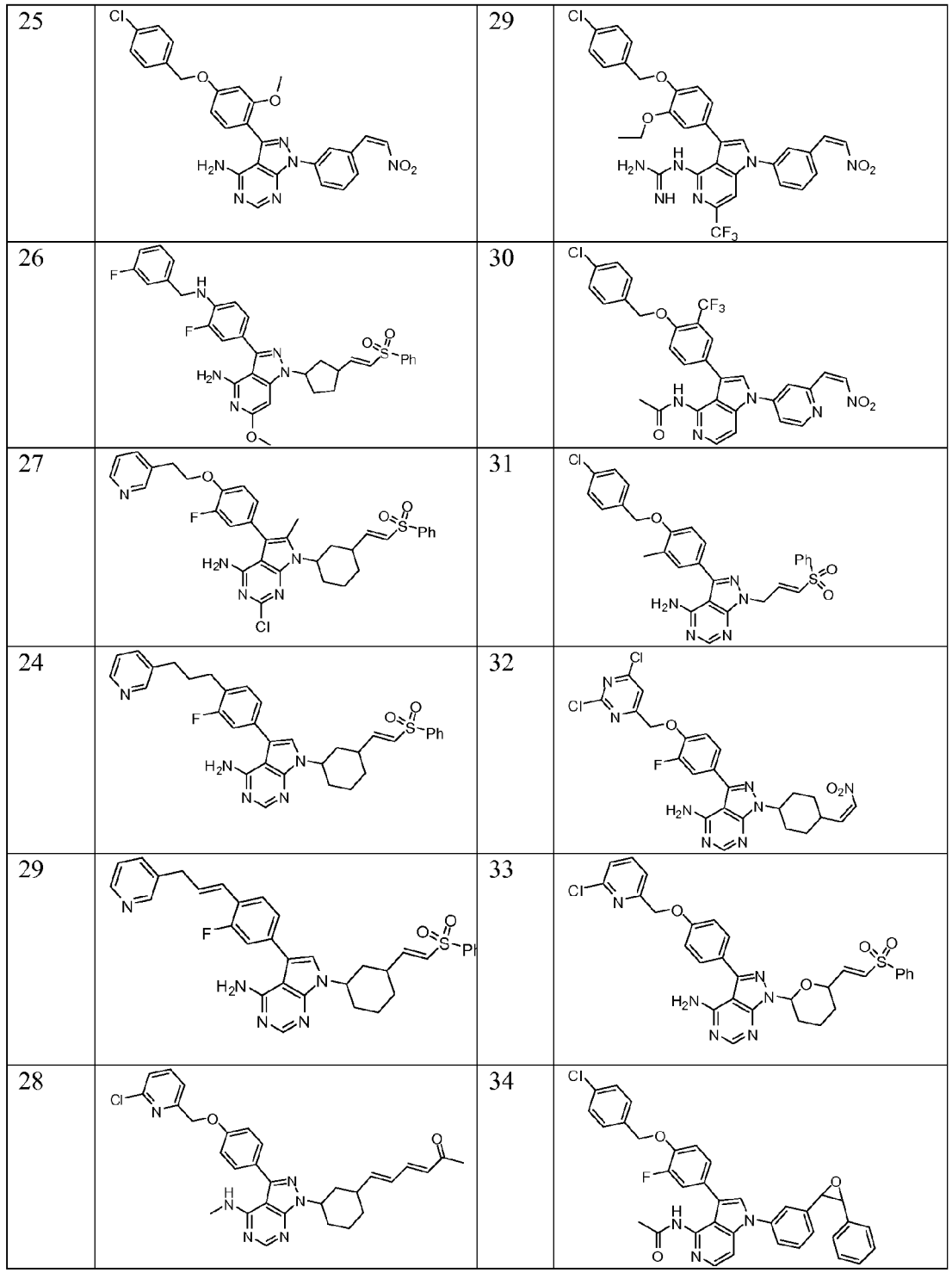

FIG. 3 presents illustrative examples of compounds described herein.

DETAILED DESCRIPTION OF THE INVENTION

Provided herein are electrophilically enhanced kinase inhibitors. In some embodiments, compounds provided herein are irreversible kinase inhibitors that comprise an electrophilic group. In specific embodiments, compounds are modified or substituted with the electrophilic group at a site that does not affect the ability of the compound to bind the ATP binding site of a kinase (e.g., tyrosine kinase). In certain embodiments, the electrophilic group is a group that undergoes nucleophilic substitution or nucleophilic addition when in proximity to a thiol, a thiolate, a cysteine residue, or any one or more of such groups. In some embodiments, provided herein are compounds that are irreversible inhibitors of cysteine containing kinases (e.g., cysteine containing kinases with a cysteine spatially near an ATP-binding site of the kinase). In some embodiments, provided herein are compounds that are irreversible inhibitors of the ErbB family of kinases. In certain embodiments, provided herein are compounds that are irreversible inhibitors of the ErbB family of kinases over the Tec family of kinases. In certain embodiments, provided herein are compounds that are irreversible inhibitors of EGFR, HER2 (ErbB2), HER4 (ErbB4), or combinations thereof. In some instances, provided herein are compounds that are irreversible inhibitors of EGFR, HER2 (ErbB2), HER4 (ErbB4), or combinations thereof, with reduced or partial inhibitory activity for BTK. In some instances, provided herein are compounds with enhanced inhibitory activity for EGFR, HER2 (ErbB2), HER4 (ErbB4), or combinations thereof, and reduced or partial inhibitory activity for BTK. Moreover, provided herein are compounds that are reversible inhibitors of kinases that do not comprise a cysteine spatially near an ATP-binding site of the kinase.

Provided in certain embodiments herein are compounds of Formula I:

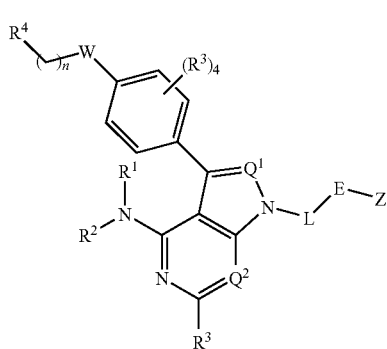

Formula I wherein:
each $R^1$ and $R^2$ is H, substituted or unsubstituted alkyl, substituted or unsubstituted heteroalkyl, $C(=O)R^5$ or $C(=NR^5)$; wherein $R^5$ is H, hydroxy, substituted or unsubstituted alkyl or substituted or unsubstituted alkoxy;

each $R^3$ is independently H, halo, hydroxy, CN, substituted or unsubstituted alkyl, substituted or unsubstituted alkoxy, or substituted or unsubstituted heteroalkyl;

each $R^4$ is independently substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

W is $—CH_2—$, $—C\equiv C—$, O, S, or $NR^1$;

n is 1-7

$Q^1$ is N or $CR^3$;

$Q^2$ is N or $CR^3$;

L is $A_p$, wherein
   each A is independently $NR^1$, $S(O)_q$, O, $C(=X)Y$, $Y(C=X)$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;

p is 0-5;

E is an electrophile;

Z is $—(Z^1)_k—Z^2$ or is absent,
   $Z^1$ is $NR^6$, O, $C(=X)Y$, $Y(C=X)$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl $Z^2$ is H, $NR^6_2$, $S(O)_qR^6$, $OR^6$, $—C(=X)YR^6$, $—Y(C=X)R^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

each $R^6$ is independently H, halo, hydroxy, alkoxy, cyano, nitro, $—C(=X)YR^7$, $—YC(=X)R^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein $R^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;

k is 0-4;

each X is independently S or O;

each Y is independently S or O;

or a pharmaceutically acceptable salt thereof.

In certain embodiments, E is an electrophile subject to nucleophilic substitution or nucleophilic addition when contacted with a thiol and/or a thiolate. In some embodiments, the electrophile is or comprises a group that is subject to nucleophilic substitution or nucleophilic addition when contacted with a thiol, a thiolate, a cysteine residue or two or more of the same. In certain embodiments, the electrophile is a Michael accepting group. In some embodiments, the electrophile is a group comprising a carbon attached to a leaving group. Any suitable leaving group is used herein, including, by way of non-limiting example, $OR^{12}$, $NR^{12}_v$, $N_3$, $SR^{12}$, or SCN; wherein $R^{12}$ is $—(S(O)_t)_u—R^{13}$; wherein each $R^{13}$ is independently H, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein t is 1-2, wherein u is 0-1, and wherein v is 2-3. In certain embodiments, the electrophilic group is a group comprising an oxirane or oxetane.

In specific embodiments, E is or comprises $-(CR^{14}R^{15})_r-(CR^8=CR^8)_q-(CR^{14}R^{15})_r-$. In certain embodiments, $R^{14}$ and $R^{15}$ are independently H, CN, $NO_2$, substituted or unsubstituted alkyl, substituted or unsubstituted aryl, or substituted or unsubstituted heteroaryl, or taken together are =S, =N—$OR^{11}$, or =O. In certain embodiments, each $R^{11}$ is independently substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl; In certain embodiments, each $R^8$ is independently H, halo, hydroxy, alkoxy, cyano, nitro, $S(O)_{1-2}R^{11}$, —C(=X)$YR^{11}$, —YC(=X)$R^{11}$, substituted or unsubstituted alkyl, substituted unsubstituted aryl, substituted or unsubstituted cycloalkyl, substituted or unsubstituted heteroaryl, substituted or unsubstituted heterocycloalkyl, substituted or unsubstituted heteroalkyl, or two $R^8$ are taken together to form a bond; In certain embodiments each r is independently 0-2; In some embodiments, each q is 0-2.

In certain embodiments, E is or comprises —$(CR^9R^{10})$—$X^2$. In certain embodiments, each $R^9$ and $R^{10}$ are independently H, halo, hydroxy, alkoxy, cyano, nitro, —C(=X)$YR^{11}$, —YC(=X)$R^{11}$, substituted or unsubstituted alkyl, substituted or unsubstituted aryl, substituted or unsubstituted cycloalkyl, substituted or unsubstituted heteroaryl, substituted or unsubstituted heterocycloalkyl, substituted or unsubstituted heteroalkyl, or is a bond to Z; or $R^9$ and $R^{10}$ taken together are =O or =S; In certain embodiments, $X^2$ is any suitable leaving group that is subject to nucleophilic substitution with a thiol, thiolate, cysteine residue, or any one or more of the same. In specific embodiments $X^2$ is halo, $OR^{12}$, $NR^{12}_v$, $N_3$, $SR^{12}$, or SCN; wherein $R^{12}$ is —$(S(O)_t)_u$—$R^{13}$; wherein each $R^{13}$ is independently H, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl. In certain embodiments $X^2$ and $R^{10}$ are taken together with the carbon to which they are bound form an oxirane or oxetane. In some embodiments t is 1-2. In some embodiments, u is 0-1. In some embodiments v is 2-3.

In some embodiments, E is or comprises —$NR^{11}$(C=O)O—; —O(C=O)$NR^{11}$—; —$CR^{11}R^{16}$(C=O)—; or —$CR^{11}R^{16}$(C=O)—, In certain embodiments, $R^{16}$ is a leaving group, e.g. a halo. In certain embodiments, $R^{11}$ is substituted or unsubstituted alkyl.

In some specific embodiments, E is or comprises —(C=O)—(CH=CH)—, or —$(SO_2)$—(CH=CH)—. In other embodiments, E is or comprises —(CH=CH)—(C=O)—, or —(CH=CH)—$(SO_2)$—. In certain embodiments, E is or comprises —CH=$C(NO_2)$—. In certain embodiments, E is or comprises —C(CN)=CH—, —CH=C(CN)—, —$C(NO_2)$=CH—. In certain embodiments, E is or comprises an oxirane ring.

In certain embodiments, $R^1$ and $R^2$ are independently H or substituted or unsubstituted alkyl. In certain embodiments, $R^1$ is H and $R^2$ is H. In some embodiments, $Q^1$ is N. In some embodiments, $Q^1$ is $CR^3$. In some embodiments, $Q^1$ is CH. In some embodiments, $Q^2$ is N. In some embodiments, $Q^2$ is $CR^3$. In some embodiments, $Q^2$ is CH. In some embodiments, $Q^1$ and $Q^2$ are CH. In some specific embodiments, $Q^1$ is N and $Q^2$ is N. In some embodiments, $R^3$ is H, halo, substituted or unsubstituted alkyl, or substituted or unsubstituted alkoxy. In some embodiments, $R^3$ is substituted or unsubstituted alkoxy. In some embodiments, $R^3$ is H, Cl or F. In some embodiments, W is —$CH_2$— or O. In some embodiments, W is NH. In some embodiments, W is O. In some embodiments, n is 1. In other embodiments, n is 2. In further embodiments, n is 3. In some other embodiments, n is 4, 5, 6 or 7. In certain specific embodiments, $R^4$ is substituted or unsubstituted aryl, or substituted or unsubstituted heteroaryl. In certain specific embodiments, $R^4$ is substituted or unsubstituted pyridinyl. In certain embodiments, $R^4$ is substituted or unsubstituted phenyl.

In certain embodiments, provided herein are compounds of Formula Ia:

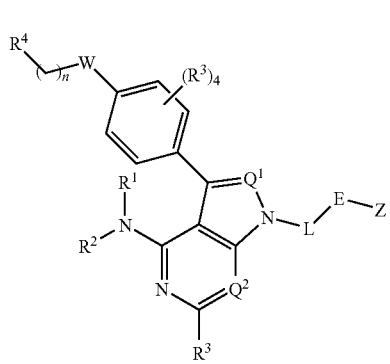

Formula Ia wherein:
$Q^1$ is N or CH;
$Q^2$ is N or CH;
In some embodiments, one A is tetrahydroquinolinyl, quinolinyl, tetrahydroisoquinolinyl, isoquinolinyl, phenyl, cyclohexyl, cyclopentyl, pyridinyl, pyrimidinyl, piperidinyl, homopiperidinyl, pyrrolidinyl, piperazinyl or morpholino and another A is alkyl or heteroalkyl. In some specific embodiments, one A is phenyl, cyclohexyl, cyclopentyl, pyridinyl, pyrimidinyl, piperidinyl, homopiperidinyl, pyrrolidinyl, piperazinyl or morpholino and another A is alkyl or heteroalkyl.

In certain specific embodiments, $Z^2$ is $NR^6_2$ and $R^6$ is substituted or unsubstituted alkyl, or substituted or unsubstituted heteroalkyl. In some embodiments, $Z^2$ is substituted or unsubstituted piperidinyl, substituted or unsubstituted pyrrolidinyl, substituted or unsubstituted piperazinyl or a substituted or unsubstituted morpholino.

In certain specific embodiments provided herein are compounds of any of FIG. 1, 2 or 3.

In some specific embodiments, provided herein are compounds of Formula II:

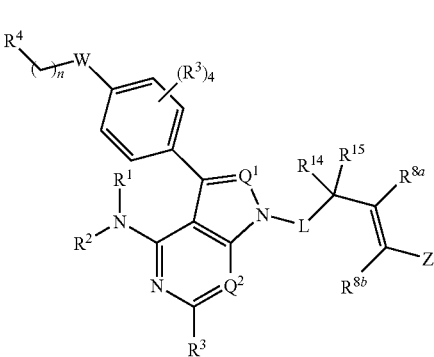

Formula II wherein
$R^3$ is H, halo, substituted or unsubstituted alkyl or substituted or unsubstituted alkoxy;

R[4] is substituted or unsubstituted aryl, substituted or unsubstituted heteroaryl, substituted or unsubstituted cycloalkyl, or substituted or unsubstituted heterocycloalkyl;

R[14] is H;

R[15] is H; or R[14] and R[15] taken together are =O;

R[8a] is H, lower alkyl, CN, $NO_2$, or $SO_2R^{11}$; and

R[8b] is H, CN, $NO_2$, or $SO_2R^{11}$.

In some embodiments, provided herein are compounds of Formula IIa:

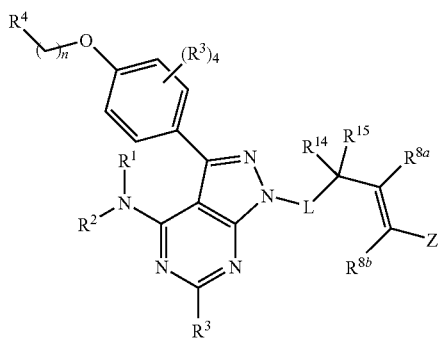

Formula IIa wherein

R[3] is H, halo, substituted or unsubstituted alkyl or substituted or unsubstituted alkoxy;

R[4] is substituted or unsubstituted aryl, substituted or unsubstituted heteroaryl, substituted or unsubstituted cycloalkyl, or substituted or unsubstituted heterocycloalkyl;

R[14] is H;

R[15] is H; or R[14] and R[15] taken together are =O;

R[8a] is H, lower alkyl, CN, $NO_2$, or $SO_2R^{11}$; and

R[8b] is H, CN, $NO_2$, or $SO_2R^{11}$

In certain embodiments, R[1], R[2], n, L and Z are as defined above. In specific embodiments, L is phenyl, cyclohexyl, cyclopentyl, pyridinyl, pyrimidinyl, piperidinyl, homopiperidinyl, pyrrolidinyl, piperazinyl or morpholino. In specific embodiments, Z is H, substituted or unsubstituted alkyl-heterocycloalkyl, substituted or unsubstituted heteroalkyl, substituted or unsubstituted alkyl, or substituted or unsubstituted alkyl-cycloalkyl.

In some embodiments, provided herein are compounds of Formula IIb:

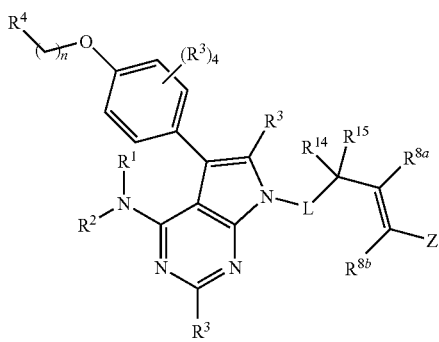

Formula IIb wherein

R[3] is H, halo, substituted or unsubstituted alkyl or substituted or unsubstituted alkoxy;

R[4] is substituted or unsubstituted aryl, substituted or unsubstituted heteroaryl, substituted or unsubstituted cycloalkyl, or substituted or unsubstituted heterocycloalkyl;

R[14] is H;

R[15] is H; or R[14] and R[15] taken together are =O;

R[8a] is H, lower alkyl, CN, $NO_2$, or $SO_2R^{11}$; and

R[8b] is H, CN, $NO_2$, or $SO_2R^{11}$.

In certain embodiments, R[1], R[2], n, L and Z are as defined above. In specific embodiments, L is phenyl, cyclohexyl, cyclopentyl, pyridinyl, pyrimidinyl, piperidinyl, homopiperidinyl, pyrrolidinyl, piperazinyl or morpholino. In specific embodiments, Z is H, substituted or unsubstituted alkyl-heterocycloalkyl, substituted or unsubstituted heteroalkyl, substituted or unsubstituted alkyl, or substituted or unsubstituted alkyl-cycloalkyl.

In some specific embodiments, provided herein are compounds of Formula IIc:

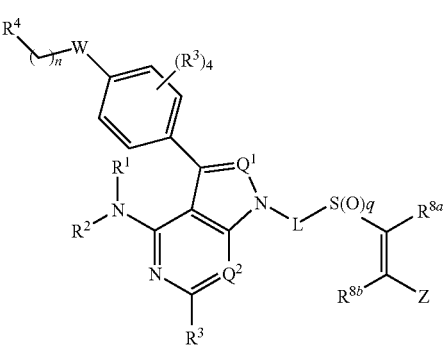

Formula IIc wherein

R[3] is H, halo, substituted or unsubstituted alkyl or substituted or unsubstituted alkoxy;

R[4] is substituted or unsubstituted aryl, substituted or unsubstituted heteroaryl, substituted or unsubstituted cycloalkyl, or substituted or unsubstituted heterocycloalkyl;

In certain embodiments, R[1], R[2], n, q, L, W and Z are as defined above. In specific embodiments, L is phenyl, cyclohexyl, cyclopentyl, pyridinyl, pyrimidinyl, piperidinyl, homopiperidinyl, pyrrolidinyl, piperazinyl or morpholino. In specific embodiments, Z is H, substituted or unsubstituted alkyl-heterocycloalkyl, substituted or unsubstituted heteroalkyl, substituted or unsubstituted alkyl, or substituted or unsubstituted alkyl-cycloalkyl.

In certain embodiments, compounds described herein have one or more chiral centers. As such, all stereoisomers are envisioned herein. In various embodiments, compounds described herein are present in optically active or racemic forms. It is to be understood that the compounds of the present invention encompasses racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contain one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

The compounds described herein, and other related compounds having different substituents are synthesized using any suitable process, e.g., using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (all of which are incorporated by reference for such disclosure). General methods for the preparation of compound as disclosed herein are modified by the use of appropriate reagents and conditions, for the introduction of the various moieties found in the formulae as provided herein. As a guide the following synthetic methods are utilized.

Compounds described herein are synthesized starting from compounds that are available from commercial sources or that are prepared using procedures outlined herein.

Formation of Covalent Linkages by Reaction of an Electrophile With a Nucleophile The compounds described herein are modified using various electrophiles and/or nucleophiles to form new functional groups or substituents. Table A entitled "Examples of Covalent Linkages and Precursors Thereof" lists selected non-limiting examples of covalent linkages and precursor functional groups which yield the covalent linkages. Table A is used as guidance toward the variety of electrophiles and nucleophiles combinations available that provide covalent linkages. Precursor functional groups are shown as electrophilic groups and nucleophilic groups.

TABLE A

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Aziridines | Thiols |
| Boronate esters | Boronates | Glycols |

TABLE A-continued

Examples of Covalent Linkages and Precursors Thereof

| Covalent Linkage Product | Electrophile | Nucleophile |
|---|---|---|
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments it is contemplated that each protective group be removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in then presence of acid- and base-protecting groups since the former are stable and are subsequently removed by metal or pi-acid catalysts. For example, an allyl-blocked carboxylic acid is deprotected with a $Pd^0$-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups are selected from:

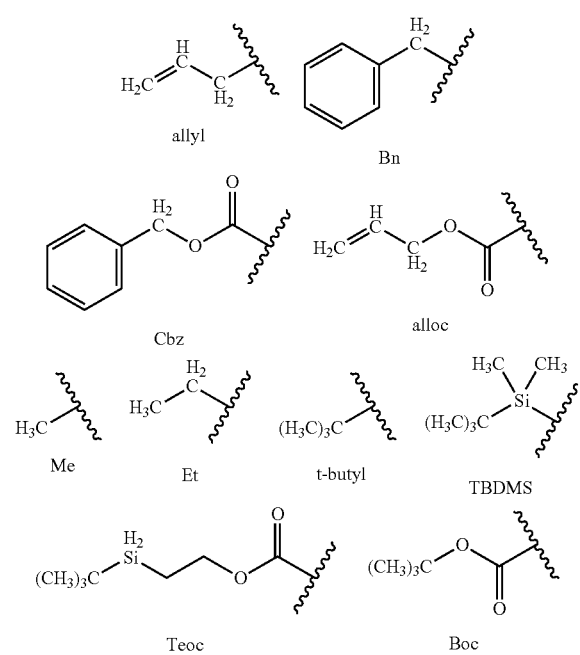

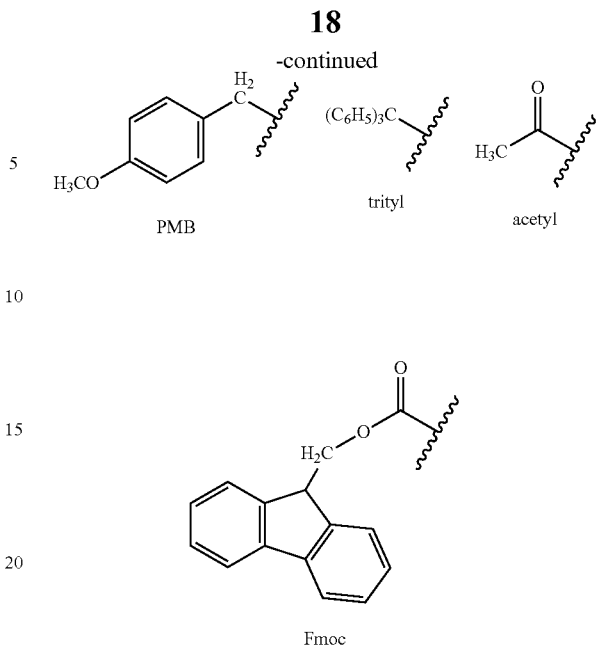

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, compounds described herein are prepared according to the process set forth in Scheme 1:

Scheme 1:

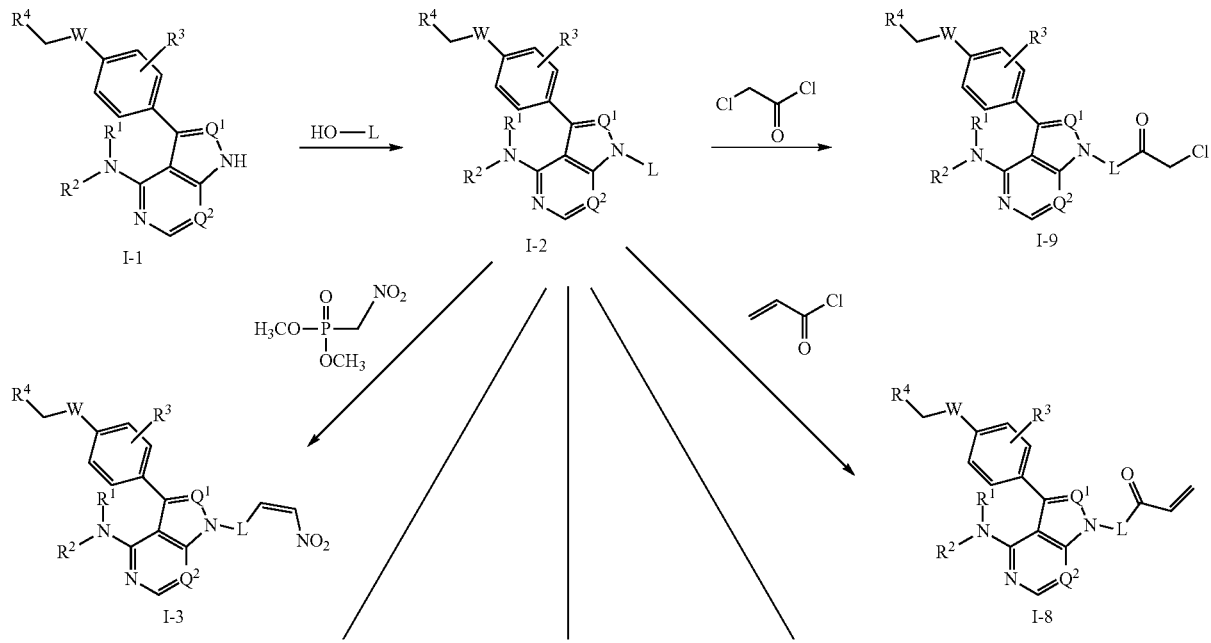

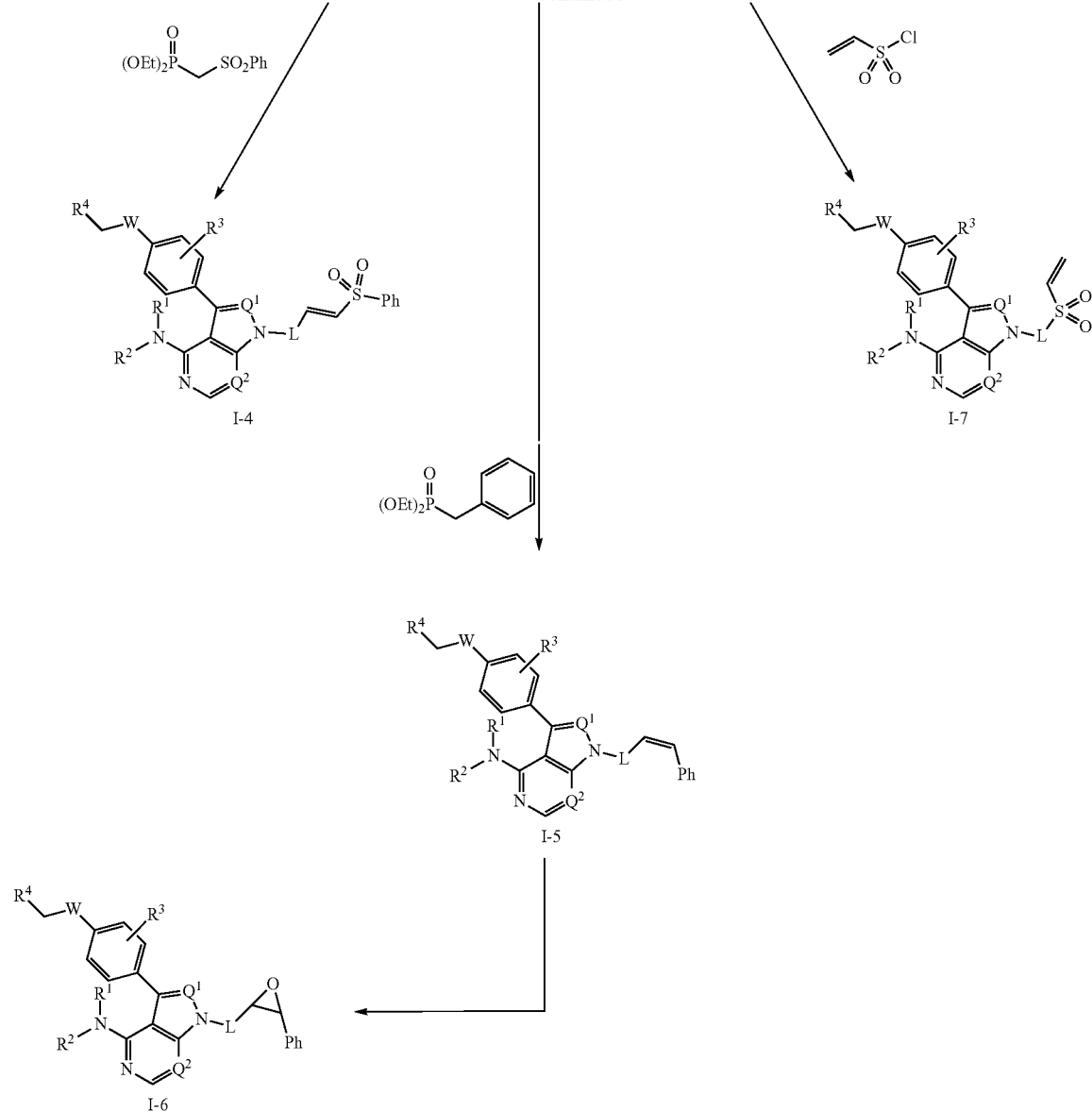

A condensation reaction, e.g., a Mitsunobu reaction, of a compound of structure I-1 with an alcohol (e.g., a substituted or unsubstituted piperidinol) provides an intermediate of structure I-2. In certain embodiments, compound I-2 is reacted with one of a variety of Wadsworth-Emmons reagents (See, e.g., U.S. Pat. No. 6,287,840) or suitable commercially available phosphonates. In some instances, reaction of a phosphonate, e.g., dimethyl nitromethylphosphonate, with an aldehyde group in compound I-2 provides a compound of structure I-3. In certain embodiments, reaction of diethyl phenylsulfonylmethylphosphonate with an aldehyde group in compound I-2 provides a compound of structure I-4. In some embodiments, reaction of diethyl benzylphosphonate with an aldehyde group in compound I-2 provides a compound of structure I-5. A compound of structure I-5 can be optionally subjected to epoxidation to provide a compound of structure I-6. In some embodiments, a Wadsworth-Emmons reagent reacts with a ketone group in compound I-2. In some embodiments, reaction of ethenesulfonyl chloride with a nucleophilic group (e.g. a primary or secondary amino group) in compound I-2 provides a compound I-5. In some embodiments, reaction of acryloyl chloride with a nucleophilic group (e.g. a primary or secondary amino group) in compound I-2 provides a compound I-8. In some embodiments, reaction of a 2-haloacetyl halide, e.g., 2—CHloroacetyl chloride, with a nucleophilic group in compound I-2 provides a compound I-9.

In specific embodiments, compounds described herein are prepared according to the process set forth in Scheme 2:

Scheme 2:

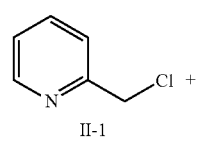

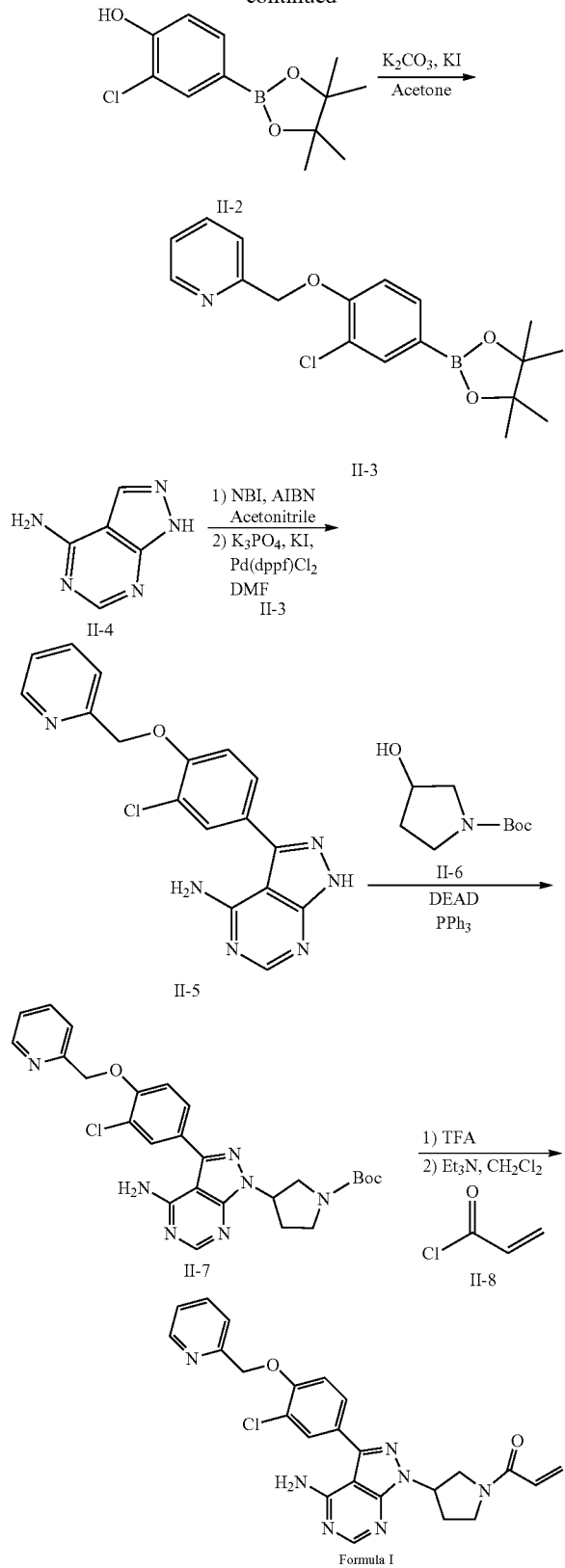

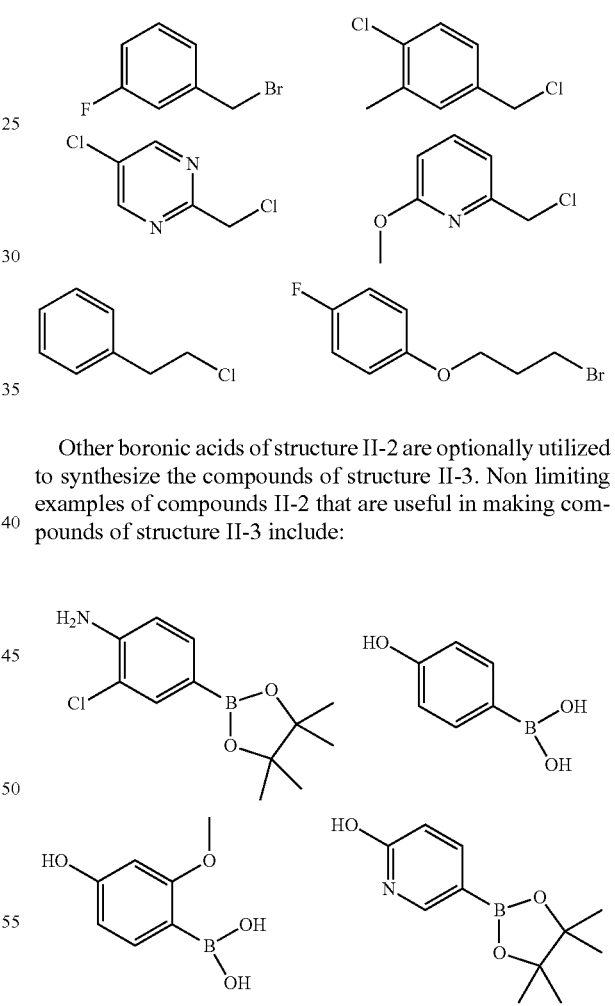

a compound of structure II-1 with a compound of structure II-2 provides a phenoxymethyl intermediate of structure II-3. Compound II-4 is subjected to a halogenation reaction, e.g., iodination, and then coupled with compound II-3 via a suitable metal mediated reaction, e,g., a Suzuki coupling, to provide compound II-5. Compound II-5 is subjected to a Mitsunobu reaction with an alcohol II-6, e.g. a substituted or unsubstituted pyrrolidinol, to provide compound II-7. Removal of the Boc protecting group in compound II-7 followed by a reaction with an electrophilic halide II-8, e.g., an acryloyl chloride, provides a compound of Formula I. In some embodiments, a sulfonyl chloride is reacted with a compound II-7 to provide compounds of Formula I.

Other compounds of structure II-1 are optionally utilized to synthesize the compounds of structure II-3. Non limiting examples of compounds II-1 that are useful in making compounds of structure II-3 include:

Other boronic acids of structure II-2 are optionally utilized to synthesize the compounds of structure II-3. Non limiting examples of compounds II-2 that are useful in making compounds of structure II-3 include:

Other alcohols are optionally utilized to synthesize the compounds of structure II-7. The alcohols are commercially available or are prepared using any suitable method. Other functional groups on the alcohols are optionally protected or deprotected using suitable methods. Non limiting examples of alcohols of structure II-5 that are useful in making compounds of structure II-7 include:

In certain embodiments, the synthesis begins with a compound of structure II-1. Such compounds are commercially available or are prepared in any suitable manner. Reaction of

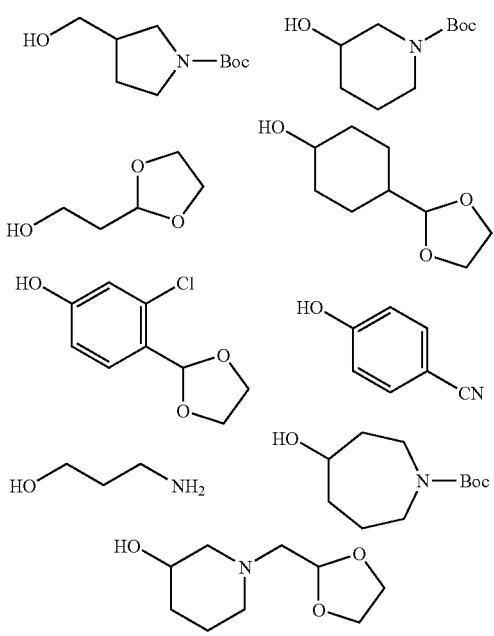

Other acyl, acryloyl or sulfonyl chlorides are optionally utilized in the syntheses of compounds of Formula I. Non limiting examples of chlorides of structure II-8 that are useful in reactions with compounds of structure II-7 include:

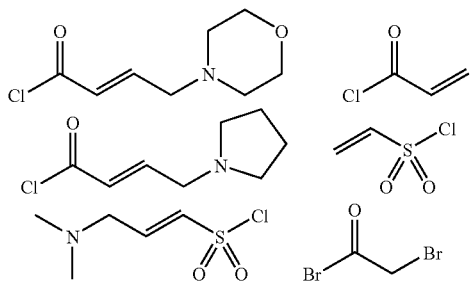

General Definitions

The term "subject", "patient" or "individual" are used interchangeably herein and refer to mammals and non-mammals, e.g., suffering from a disorder described herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated, and/or the eradication or amelioration of one or more of the physiological symptoms associated with the underlying disorder such that an improvement is observed in the patient.

The terms "prevent," "preventing" or "prevention," and other grammatical equivalents as used herein, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at risk of developing a particular disease, to a patient reporting one or more of the physiological symptoms of a disease, or to a patient at risk of reoccurrence of the disease.

Where combination treatments or prevention methods are contemplated, it is not intended that the agents described herein be limited by the particular nature of the combination. For example, the agents described herein are optionally administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent. Furthermore, combination treatments are optionally administered separately or concomitantly.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to a patient simultaneously in the form of a single entity or dosage. The term "non-fixed combination" means that at least one of the agents described herein, and at least one co-agent, are administered to a patient as separate entities either simultaneously, concurrently or sequentially with variable intervening time limits, wherein such administration provides effective levels of the two or more agents in the body of the patient. In some instances, the co-agent is administered once or for a period of time, after which the agent is administered once or over a period of time. In other instances, the co-agent is administered for a period of time, after which, a therapy involving the administration of both the co-agent and the agent are administered. In still other embodiments, the agent is administered once or over a period of time, after which, the co-agent is administered once or over a period of time. These also apply to cocktail therapies, e.g. the administration of three or more active ingredients.

As used herein, the terms "co-administration", "administered in combination with" and their grammatical equivalents are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Administration techniques that are optionally employed with the agents and methods described herein are found in sources e.g., Goodman and Gilman, The Pharmacological Basis of Therapeutics, current ed.; Pergamon; and Remington's, Pharmaceutical Sciences (current edition), Mack Publishing Co., Easton, Pa. In certain embodiments, the agents and compositions described herein are administered orally.

The terms "selective for" or "selectively binding" are used interchangeably. In some embodiments, a selective compound or a compound that binds selectively is a compound that is about 50% more active for a particular kinase (e.g., EGFR, ErbB2 or ErbB4) or a group of kinases (e.g., ErbB kinases) or some members of a group of kinases (e.g., EGFR and ErbB2) than another kinase or group of kinases (e.g. Tec kinases). In some embodiments, a selective compound or a compound that binds selectively is a compound that is about 60%, about 70%, about 80%, about 90%, or about 100% more active for a particular kinase (e.g., EGFR, ErbB2 or ErbB4) or a group of kinases (e.g., ErbB kinases) or some members of a group of kinases (e.g., EGFR and ErbB2) than another kinase or group of kinases (e.g. Tec kinases). In some embodiments, a selective compound or a compound that binds selectively is a compound that is about 50% more active against non-BTK kinases when compared with activity against BTK. In some embodiments, a selective compound is about 60%, about 70%, about 80%, about 90%, or about 100% more active against non-BTK kinases when compared with activity against BTK. In some embodiments, a selective compound or a compound that binds selectively is a compound that is 50% more active against ErbB kinases (e.g., EGFR, ErbB2, ErbB4) when compared with activity against BTK. In some embodiments, a selective compound is about 60%, about 70%, about 80%, about 90%, or about 100% more active against ErbB kinases (e.g., EGFR, ErbB2, ErbB4) when compared with activity against BTK.

The terms "HER2" and "ErbB2" are used interchangeably. The terms "HER4" and "ErbB4" are used interchangeably. The terms "EFGR" and "ErbB1" are used interchangeably.

The term "ErbB kinaseS" refers to the Epidermal Growth Factor (EGF) family of receptor tyrosine kinases (RTKs) that includes, e.g., EGFR/ErbB1/HER1, ErbB2/Neu/HER2, ErbB3/HER3, and/or ErbB4/HER4.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "carrier" as used herein, refers to relatively non-toxic chemical agents that, in certain instances, facilitate the incorporation of an agent into cells or tissues.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p-tolunenesulfonate, mesylate and the like. Furthermore, pharmaceutically acceptable salts include, by way of non-limiting example, alkaline earth metal salts (e.g., calcium or magnesium), alkali metal salts (e.g., sodium or potassium), ammonium salts and the like.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halo, alkoyl, alkoyloxo, isocyanato, thiocyanato, isothiocyanato, nitro, haloalkyl, haloalkoxy, fluoroalkyl, amino, alkyl-amino, dialkyl-amino, amido.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl.

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NHR or —NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom.

Aryl rings disclosed herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Illustrative examples of cycloalkyl groups include, but are not limited to, the following moieties:

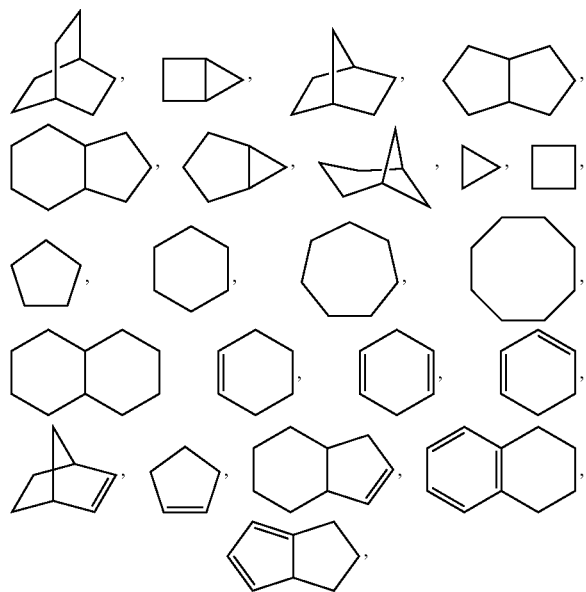

and the like. Monocyclic cycloalkyls include, but are not limited to, cyclopropyl, cyclobutyl, cyclopentyl, cyclohexyl, cycloheptyl, and cyclooctyl.

The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Illustrative examples of heteroaryl groups include the following moieties:

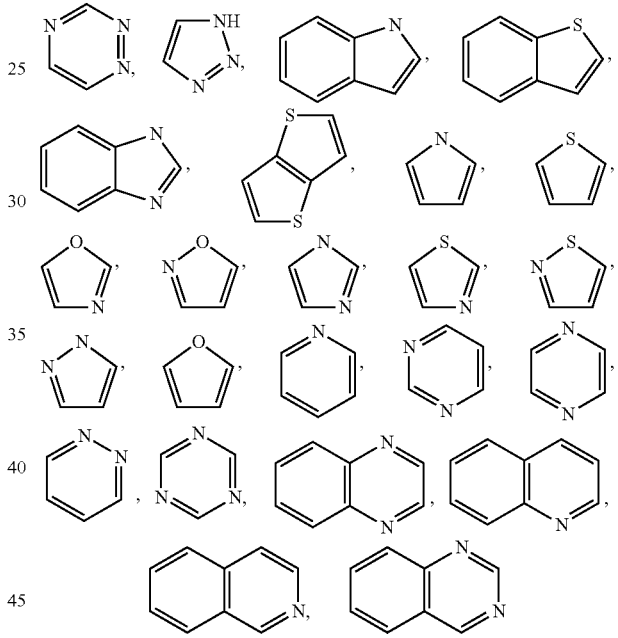

and the like.

A "heteroalicyclic" group or "heterocyclo" group refers to a cycloalkyl group, wherein at least one skeletal ring atom is a heteroatom selected from nitrogen, oxygen and sulfur. In various embodiments, the radicals are with an aryl or heteroaryl. Illustrative examples of heterocyclo groups, also referred to as non-aromatic heterocycles, include:

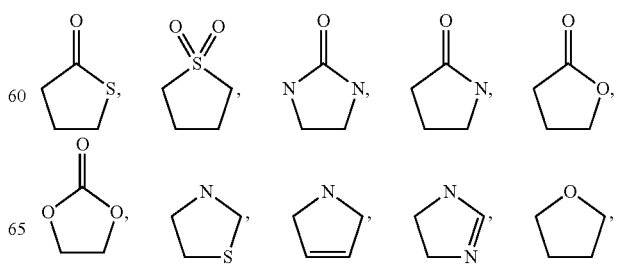

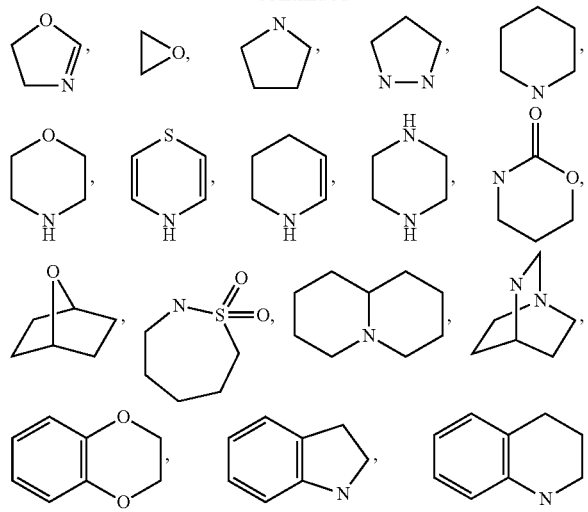

and the like. The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$,—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In some embodiments, up to two heteroatoms are consecutive, such as, by way of example, —CH$_2$—NH—OCH$_3$ and —CH$_2$—O—Si(CH$_3$)$_3$.

A "cyano" group refers to a —CN group.

An "isocyanato" group refers to a —NCO group.

A "thiocyanato" group refers to a —CNS group.

An "isothiocyanato" group refers to a —NCS group.

"Alkoyloxy" refers to a RC(=O)O— group.

"Alkoyl" refers to a RC(=O)— group.

Methods

In certain embodiments, provided herein is a method of inhibiting, reducing the activity of, knocking down, or modulating the activity of a kinase by contacting the kinase with an effective amount of any compound described herein. In some embodiments, the kinase is a cysteine containing kinase. In certain embodiments, the method provides a method of irreversibly inhibiting, reducing the activity of, knocking down, or modulating the activity of a kinase by contacting the kinase with an effective amount of any compound described herein.

In specific embodiments, the kinase comprises a cysteine residue near an ATP-binding site of the kinase. In more specific embodiments, the cysteine residue is in close spatial proximity to an ATP-binding site of the kinase. In some embodiments, the kinase comprising a cysteine residue near an ATP-binding site includes, by way of non-limiting example, BTK, BMX, TEC, TXK, ITK, EGFR, ErbB2, ErbB4, JAK3, BLK, or the like. In some embodiments, the kinase comprising a cysteine residue near an ATP-binding site includes, by way of non-limiting example, BMX, TEC, TXK, ITK, EGFR, ErbB2, ErbB4, JAK3, BLK, or the like. In some embodiments, the kinase is a tyrosine kinase. In more specific embodiments, the tyrosine kinase is a ErbB family kinase. In some specific embodiments, the tyrosine kinase comprises a cysteine residue near an ATP-binding site of the tyrosine kinase. In more specific embodiments, the cysteine residue is in close spatial proximity to an ATP-binding site of the tyrosine kinase. In some embodiments, compounds described herein are also utilized in methods of inhibiting, reducing the activity of, or modulating the activity of ErbB family kinases over Tec family kinases (e.g., BTK). In some embodiments, the method is performed in vitro, or in vivo. In some embodiments, when performed in vivo, the individual to which the compound is administered has been diagnosed with a disease or disorder disclosed herein (e.g., a kinase mediated disorder disclosed herein).

In some embodiments, provided herein is a method of binding a cysteine containing kinase to a compound of Formula I comprising contacting the kinase with the compound of Formula I. In some embodiments, the process of binding the compound to the kinase comprises forming a covalent bond between the kinase and the compound of Formula I. In specific embodiments, the process of binding is an irreversible process. In specific embodiments, the kinase comprises a cysteine residue near an ATP-binding site of the kinase. In more specific embodiments, the cysteine residue is in close spatial proximity to an ATP-binding site of the kinase. In some embodiments, the kinase comprising a cysteine residue near an ATP-binding site includes, by way of non-limiting example, BTK, BMX, TEC, TXK, ITK, EGFR, ErbB2, ErbB4, JAK3, BLK, or the like. In some embodiments, the kinase comprising a cysteine residue near an ATP-binding site includes, by way of non-limiting example, BMX, TEC, TXK, ITK, EGFR, ErbB2, ErbB4, JAK3, BLK, or the like. In some embodiments, the kinase is a tyrosine kinase. In more specific embodiments, the tyrosine kinase is a ErbB family kinase. In specific embodiments, the kinase is EGFR, ErbB2, ErbB4, or a combination thereof. In some specific embodiments, the tyrosine kinase comprises a cysteine residue near an ATP-binding site of the tyrosine kinase. In more specific embodiments, the cysteine residue is in close spatial proximity to an ATP-binding site of the tyrosine kinase. In some embodiments, the method is performed in vitro, or in vivo. In some embodiments, when performed in vivo, the individual to which the compound is administered has been diagnosed with a disease or disorder disclosed herein (e.g., a ErbB kinase mediated disorder disclosed herein).

In some embodiments, provided herein is a method of decreasing the dose necessary of a therapeutic agent to treat a kinase mediated disorder (e.g. an ErbB kinase mediated disorder) in an individual in need thereof by replacing a Compound 100 treatment with a treatment comprising administering to the individual a therapeutically effective amount of any compound described herein. In some embodiments, provided herein is also a method of treating a disease or disorder mediated by a kinase by administering to an individual in need thereof a therapeutically effective amount of a compound described herein, wherein the therapeutically effective amount is less than a therapeutically effective amount of Compound 100 (by weight and/or molar amount). In some embodiments, provided herein is a method of treating a kinase mediated disorder (e.g. an ErbB kinase mediated disorder) that is refractory or non-responsive to treatment with a compound 100. In some embodiments, provided herein is a method of treating a kinase mediated disorder (e.g. an ErbB kinase mediated disorder) that is refractory or non-responsive to treatment with a compound 100 by replacing a Compound 100 treatment with a treatment comprising administering to the individual a therapeutically effective amount of any compound described herein. In specific embodiments, the kinase comprises a cysteine residue near an ATP-binding site of the kinase. In more specific embodiments, the cysteine residue is in close spatial proximity to an ATP-binding site of the kinase. In some embodiments, the kinase comprising a cysteine residue near an ATP-binding site includes, by way of non-limiting example, BTK, BMX, TEC, TXK, ITK, EGFR, ErbB2, ErbB4, JAK3, BLK, or the like. In some embodiments, the kinase comprising a cysteine residue near an ATP-binding site includes, by way of non-limiting example, BMX, TEC, TXK, ITK, EGFR, ErbB2, ErbB4, JAK3, BLK, or the like. In some embodiments, the kinase is a tyrosine kinase. In some embodiments, the kinase is a receptor tyrosine kinase. In more specific embodiments, the tyrosine kinase is a ErbB family kinase. In specific embodiments, the kinase is EGFR, ErbB2, ErbB4, or a combination thereof. In some specific embodiments, the tyrosine kinase comprises a cysteine residue near an ATP-binding site of the tyrosine kinase. In more specific embodiments, the cysteine residue is in close spatial proximity to an ATP-binding site of the tyrosine kinase. In some embodiments, the individual to which the compound is administered has been diagnosed with a disease or disorder disclosed herein (e.g., a ErbB kinase mediated disorder disclosed herein).

In some embodiments, provided herein is a reduced side effect method of treating a a kinase mediated disorder (e.g. an ErbB kinase mediated disorder) in an individual in need thereof by administering to the individual a therapeutically effective amount of any compound described herein. In certain embodiments, the method ameliorates or reduces side effects caused by sustained BTK inhibition (e.g., nausea, allergic reaction with passive cutaneous anaphylaxis or compromised T-cell-independent immune response) In some instances this is achieved by administering a compound described herein that selectively inhibits an ErbB kinase relative to BTK. In certain instances a reduction in side effects is achieved by administering a reduced amount of an irreversible kinase inhibitor compound described herein compared to a reversible kinase inhibitor (e.g. Compound 100). In certain instances a reduction in side effects is achieved by replacing a Compound 100 treatment with a treatment comprising any compound described herein. In certain instances, a reduction in side effects is achieved by administering an irreversible kinase inhibitor compound described herein to an individual with a kinase-mediated disorder that is refractory or non-responsive to high doses of a reversible kinase inhibitor (e.g. Compound 100). In some embodiments, provided herein is a method of treating a disease or disorder mediated by a kinase by administering to an individual in need thereof a therapeutically effective amount of a compound described herein, wherein the administered amount is more than the maximum tolerated dose of a Compound 100 (by weight and/or molar amount), the method described herein resulting in equivalent or reduced side effects than a therapeutically effective amount of a Compound 100. In certain embodiments, a reduction in side effects due to sustained BTK inhibition (e.g., nausea, allergic reaction with passive cutaneous analphylaxis or compromised T-cell-independent immune response) is achieved by co-administration of any compound described herein with a reversible kinase inhibitor (e.g. Compound 100). In specific embodiments, the kinase comprises a cysteine residue near an ATP-binding site of the kinase. In more specific embodiments, the cysteine residue is in close spatial proximity to an ATP-binding site of the kinase. In some embodiments, the kinase comprising a cysteine residue near an ATP-binding site includes, by way of non-limiting example, BTK, BMX, TEC, TXK, ITK, EGFR, ErbB2, ErbB4, JAK3, BLK, or the like. In some embodiments, the kinase comprising a cysteine residue near an ATP-binding site includes, by way of non-limiting example, BMX, TEC, TXK, ITK, EGFR, ErbB2, ErbB4, JAK3, BLK, or the like. In some embodiments, the kinase is a tyrosine kinase. In some embodiments, the kinase is a receptor tyrosine kinase. In more specific embodiments, the tyrosine kinase is a ErbB family kinase. In specific embodiments, the kinase is EGFR, ErbB2, ErbB4, or a combination thereof. In some specific embodiments, the tyrosine kinase comprises a cysteine residue near an ATP-binding site of the tyrosine kinase. In more specific embodiments, the cysteine residue is in close spatial proximity to an ATP-binding site of the tyrosine kinase. In some embodiments, the individual to which the compound is administered has been diagnosed with a disease or disorder disclosed herein (e.g., a ErbB kinase mediated disorder disclosed herein).

In certain embodiments, provided herein is a method of administering an effective amount of any compound described herein to an individual in need thereof for the treatment of a disease or disorder mediated by a kinase (e.g. an ErbB kinase mediated disorder). In some embodiments, the kinase is a cysteine containing kinase. In specific embodiments, the kinase comprises a cysteine residue near an ATP-binding site of the kinase. In more specific embodiments, the cysteine residue is in close spatial proximity to an ATP-binding site of the kinase. In some embodiments, the kinase comprising a cysteine residue near an ATP-binding site includes, by way of non-limiting example, BTK, BMX, TEC, TXK, ITK, EGFR, ErbB2, ErbB4, JAK3, BLK, or the like. In some embodiments, the kinase comprising a cysteine residue near an ATP-binding site includes, by way of non-limiting example, BMX, TEC, TXK, ITK, EGFR, ErbB2, ErbB4, JAK3, BLK, or the like. In some embodiments, the kinase is a tyrosine kinase. In more specific embodiments, the tyrosine kinase is a ErbB family kinase. In specific embodiments, the kinase is EGFR, ErbB2, ErbB4, or a combination thereof. In some specific embodiments, the tyrosine kinase comprises a cysteine residue near an ATP-binding site of the tyrosine kinase. In more specific embodiments, the cysteine residue is in close spatial proximity to an ATP-binding site of the tyrosine kinase. In some embodiments, compounds described herein are also utilized in methods treating diseases or disorders that are refractory to treatment with reversible kinase inhibitors.

Kinases play critical roles in signaling pathways controlling fundamental cellular processes such as proliferation, differentiation, and death (apoptosis). Abnormal kinase activity is implicated in a wide range of diseases, including multiple cancers and autoimmune and inflammatory diseases.

Diseases mediated by receptor kinase activity include, but are not limited to, diseases characterized in part by abnormal levels of cytokines (i.e., inflammation), cell proliferation (e.g. cancer), programmed cell death (apoptosis), cell migration and invasion, and angiogenesis associated with tumor growth.

In some embodiments, disclosed herein are methods and compositions for the modulation, and treatment of immune, inflammatory, respiratory, autoimmune, cardiovascular, neuronal, ischemic, hematological and proliferative disorders. In certain embodiments, such disorders are treated by administering a therapeutically effective amount of a compound described herein to an individual in need thereof (e.g., an individual diagnosed with one or more of such disorders).

Immune disorders include, but are not limited to, chronic inflammatory diseases and autoimmune disorders, such as Crohn's disease, reactive arthritis, including Lyme disease, systemic lupus erythematosus (SLE), insulin-dependent diabetes, organ—Specific auto immunity, Hashimoto's thyroiditis and Grave's disease, contact dermatitis, psoriasis, organ transplant rejection, graft rejection, graft versus host disease, sarcoidosis, atopic conditions, gastrointestinal allergies, including food allergies, pancreatitis, inflammatory bowel disease, eosinophilia, conjunctivitis, glomerular nephritis, multiple vasculitides, myasthenia gravis, certain pathogen susceptibilities such as helminthic infections (e.g., leishmaniasis), certain viral infections, including HIV, and bacterial infections, including tuberculosis and lepromatous leprosy.

Respiratory disorders include, but are not limited to, apnea, asthma, particularly bronchial asthma, allergy, including allergic rhinitis, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Hematologic disorders include but are not limited to anemias including sickle cell and hemolytic anemia, erythrocytosis, hemophilias including types A and B, leukemias, thalassemias, spherocytosis, Von Willebrand disease, chronic granulomatous disease, glucose-6-phosphate dehydrogenase deficiency, thrombosis, clotting factor abnormalities and deficiencies including factor VIII and IX deficiencies, hemarthrosis, hematemesis, hematomas, hematuria, hemochromatosis, hemoglobinuria, hemolytic-uremic syndrome, thrombocytopenias including HIV-associated thrombocytopenia, hemorrhagic telangiectasia, idiopathic thrombocytopenic purpura, thrombotic microangiopathy, hemosiderosis.

Proliferative disorders include and are not limited to cancer, including breast and ovarian cancers, epithelial cancers such as gastric adenocarcinoma, prostate cancer, lung cancer, head and neck cancer, bladder cancer, melanoma, oesophageal cancer, lymphoma, including B-cell and Hodgkins lymphoma, brain tumors, colorectal cancer, renal cancer, squamous cell cancer, glioblastoma, Kaposi's sarcoma, multiple myeloma, and leukemia (e.g. myeloid, chronic myeloid, acute lymphoblastic, chronic lymphoblastic, and other leukemias and hematological cancers).

Neuronal disorders include and are not limited to Alzheimers disease, Parkinson's disease, dementia, Huntington's disease, multiple sclerosis, neuronal ceroid lipofuscinosis, autism and epilepsy.

Ischemic disorders include and are not limited to liver ischemia, myocardial infarction and reperfusion injury.

Cardiovascular disorders include heart failure, hypertension, atrial fibrillation, dilated cardiomyopathy, idiopathic cardiomyopathy, or angina.

Human epidermal growth factor (EGF) is a 53 amino acid, single—CHain polypeptide (Mr 6216 daltons), which exerts biologic effects by binding to a specific cell membrane epidermal growth factor receptor (EGFR/ErbB-1). In certain instances, EGFR mediated disorders include cancers, such as, by way of non-limiting example, breast cancer, prostate cancer, lung cancer, head and neck cancer, bladder cancer, melanoma, and brain tumors (Khazaie, K., et al. R. B. Cancer & Metastasis Reviews 1993, 12, 255).

HER4/ErbB4 is a receptor protein tyrosine kinase belonging to the ErbB family. Increased ErbB4 expression closely correlates with certain carcinomas of epithelial origin, including breast adenocarcinomas (Plowman et al., Proc. Natl. Acad. Sci. USA 90:1746-1750 [1993]; Plowman et al., Nature 366:473-475 [1993]). Other members of the ErbB family of receptor tyrosine kinases include: epidermal growth factor receptor (EGFR), ErbB2 (HER2/neu), and ErbB3 (HER3). HER4 acts, in the absence of HER2, as a mediator of antiproliferative and differentiative response in human breast cancer cell lines. (Sartor et al., Mol. Cell Biol. 21:4265-75 (2001). In some instances, ErbB4/ErbB2 mediated disorders include epithelial malignancies such as breast cancer.

Smooth muscle cells from a variety of organs such as the heart and the urinary bladder possess EGF receptors. Various EGF ligands act as potent mitogens and stimulate proliferation of smooth muscle cells often resulting in thickening of the wall and ultimately stenosis. EGFR mediated disorders include disorders caused by excessive proliferation of vascular smooth muscle cells (VSMC) such as vascular stenosis, restenosis resulting from angioplasy or surgery or stent implants, atherosclerosis, transplant atherosclerosis and hypertension (reviewed in Casterella and Teirstein, Cardiol. Rev. 7: 219-231 [1999]; Andres, Int. J. Mol. Med. 2: 81-89 [1998]; and Rosanio at al, Thromb. Haemost. 82 [suppl 1]: 164-170 [1999]). Excessive proliferation of VSMC can cause decreased blood supply to tissues and may also cause necrosis and/or inflammatory response leading to severe damage. For example, myocardial infarction occurs as a result of lack of oxygen and local death of heart muscle tissues.

EGF receptor mediated excessive proliferation of urinary bladder smooth muscle cells causes obstruction and hyperplasia of the bladder. Infantile hypertrophic pyloric stenosis (IHPS), which causes functional obstruction of the pyloric canal with hypertrophy and hyperplasia of the pyloric smooth muscle cells, may be mediated by EGFR (Due and Puri, Pediatr. Res. 45: 853-857 [1999]).

The obstructive airway diseases are yet another group of diseases with underlying pathology involving EFG receptor mediated smooth muscle cell proliferation. One example of this group is asthma which manifests in airway inflammation and bronchoconstriction.

The Src-family of tyrosine kinase plays a critical role in blood cell function. Many members of the Src-family of tyrosine kinases are found exclusively or primarily in blood cells, and inhibitors of Src kinases block leukemic cell growth (Corey et al., Leukemia. 1999;13(6):855-61). Disorders mediated by Src tyrosine kinase may also include, by way of non-limiting example, hematologic tumors, and solid tumors.

Excessive tyrosine kinase activity is also associated with inflammatory and autoimmune diseases. In some instances, Src (e.g., Lyn, Hck, Lck, Fgr, and Blk) mediated disorders may include, by way of non-limiting example, allergic diseases, autoimmunity, and transplantation rejection.

In certain instances, the Aβ peptide in senile plaques activates Src tyrosine kinases. In certain instances, Src mediated disorders may include, by way of non-limiting example, CNS disorders including, but not limited to, Parkinsons Disease and chronic pain. Increased neuronal Src kinase activity induces epileptiform discharges. The frequency of the epileptiform discharges is decreased by the addition of an inhibitor of the Src family of tyrosine kinases. Additional Src mediated disorders include epilepsy and other disorders related to NMDA receptor function (Sanna et al., Proc Natl Acad Sci USA. 2000, 18;97(15):8653-7).

Herpesviridae, papovaviridae, and retroviridae interact with non-receptor tyrosine kinases and use them as signaling intermediates. For example, the HIV-1 Nef protein interacts with members of the Src family of tyrosine kinases. In some instances, the Src tyrosine kinases mediate diseases caused by viral proteins such as polyomavirus middle-T antigens, Epstein-Barr virus LMP2A, and herpesvirus saimiri Tip (Dunant and Ballmer-Hofer, Cell Signal. 1997;9(6):385-93).

The Janus kinases (JAK1, JAK2 and JAK3) are tyrosine kinases that play a critical role in cytokine signaling and are implicated in the mediation of many abnormal immune responses such as allergies, asthma, autoimmune diseases such as transplant rejection, rheumatoid arthritis, amyotrophic lateral sclerosis and multiple sclerosis, solid and hematologic malignancies such as leukemias and lymphomas, and proliferative disorders such as erythrocytosis (Frank Mol. Med. 5: 432 456 (1999) & Seidel, et al, Oncogene 19: 2645 2656 (2000)).

Bruton's Tyrosine Kinase (Btk) is a member of the Tec family of tyrosine kinases, and is a critical regulator of early B-cell development as well as mature B-cell activation, signaling and survival. B-cell signaling through the B-cell receptor (BCR) leads to a wide range of biological outputs. Aberrant BCR-mediated signaling can cause disregulated B-cell proliferation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation. In certain instances, sustained inhibition of BTK leads to side effects such as e.g. compromised T-cell-independent immune responses.

Inhibition of Btk activity is useful for the treatment of autoimmune and/or inflammatory diseases such as: SLE, rheumatoid arthritis, multiple vasculitides, idiopathic thrombocytopenic purpura (ITP), myasthenia gravis, and asthma. In addition, Btk has been reported to play a role in apoptosis; inhibition of Btk activity is useful for the treatment of B-cell lymphoma and leukemia.

Administration of a compound described herein is achieved in any suitable manner including, by way of non-limiting example, by oral, parenteral (e.g., intravenous, subcutaneous, intramuscular), intranasal, buccal, topical, rectal, or transdermal administration routes.

In certain embodiments, a compound or a composition comprising a compound described herein is administered for prophylactic and/or therapeutic treatments. In therapeutic applications, the compositions are administered to an individual already suffering from a disease or condition, in an amount sufficient to cure or at least partially arrest the symptoms of the disease or condition. In various instances, amounts effective for this use depend on the severity and course of the disease or condition, previous therapy, the individual's health status, weight, and response to the drugs, and the judgment of the treating physician.

In prophylactic applications, compounds or compositions containing compounds described herein are administered to an individual susceptible to or otherwise at risk of a particular disease, disorder or condition. In certain embodiments of this use, the precise amounts of compound administered depend on the individual's state of health, weight, and the like. Furthermore, in some instances, when a compound or composition described herein is administered to an individual, effective amounts for this use depend on the severity and course of the disease, disorder or condition, previous therapy, the individual's health status and response to the drugs, and the judgment of the treating physician.

In certain instances, wherein following administration of a selected dose of a compound or composition described herein, an individual's condition does not improve, upon the doctor's discretion the administration of a compound or composition described herein is optionally administered chronically, that is, for an extended period of time, including throughout the duration of the individual's life in order to ameliorate or otherwise control or limit the symptoms of the individual's disorder, disease or condition.

In certain embodiments, an effective amount of a given agent varies depending upon one or more of a number of factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In some embodiments, doses administered include those up to the maximum tolerable dose. In certain embodiments, about 0.02-5000 mg per day, from about 1-1500 mg per day, about 1 to about 100 mg/day, about 1 to about 50 mg/day, or about 1 to about 30 mg/day, or about 5 to about 25 mg/day of a compound described herein is administered. In various embodiments, the desired dose is conveniently be presented in a single dose or in divided doses administered simultaneously (or over a short period of time) or at appropriate intervals, for example as two, three, four or more sub-doses per day.

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. In certain embodiments, data obtained from cell culture assays and animal studies are used in formulating a range of dosage for use in human. In specific embodiments, the dosage of compounds described herein lies within a range of circulating concentrations that include the $ED_{50}$ with minimal toxicity. The dosage optionally varies within this range depending upon the dosage form employed and the route of administration utilized.

Combinations

In certain instances, provided herein are combination compositions and/or therapies comprising a compound of any of Formulas I, Ia, II, IIa, IIb or IIc, and an additional therapeutic agent. In specific embodiments, the additional therapeutic agent is an anti-cancer agent, an anti-inflammatory agent, or an immunosuppressant.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g, from more than zero weeks to less than four weeks. In some embodiments, the additional therapeutic agent is utilized to achieve remission (partial or complete) of a cancer, whereupon the therapeutic agent described herein (e.g., a compound of any one of Formulas I, Ia, II, IIa, IIb or IIc) is subsequently administered. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy disclosed herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two—Step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

In certain embodiments, therapeutic agents are combined with or utilized in combination with one or more of the following therapeutic agents in any combination: immunosuppressants or anti-cancer therapies (e.g., radiation, surgery or anti-cancer agents).

In some embodiments, the additional therapeutic agent is an anti-inflammatory agent. Specific anti-inflammatory agents include, by way of non-limiting example, steroids and NSAIDs. Non—Steroidal anti-inflammatory drugs (NSAIDs) include, by way of non-limiting example, salicylates, amoxiprin, benorylate, choline magnesium salicylate, diflunisal, ethenzamide, faislamine, methyl salicylate, magnesium salicylate, salicyl salicylate, salicylamide, aspirin, arylalkoinic acids, diclofenac, aceclofenac, acemethacin, alclofenac, bromfenac, etodolac, indomethacin, nabumetone, oxametacin, proglumetacin, sulindac, tolmetin, 2-arylpropionic acids, profens, alminoprofen, benoxaprofen, carprofen, dexibuprofen, dexketoprofen, fenbufen, fenoprofen, flunoxaprofen, flurbiprofen, ibupromax, indoprofen, ketoprofen, ketorolac, loxoprofen, naproxen, oxaprozin, pirprofen, suprofen, tiaprofenic acid, ibuprofen, N-arylanthranilic acids, fenamic acids, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, sulfinpyrazone, oxicams, piroxicam, droxicam, lornoxicam, meloxicam, tenoxicam, celecoxib, etoricoxib, lumiracoxib, parecoxib, rofecoxib, valdecoxib, naproxen, or the like. Steroid include, by way of non-limiting example, corticosteroids, hydrocortisone, cortisone acetate, prednisone, prednisolone, methylprednisolone, dexamethasone, betamethasone, triamcinolone, beclometasone, fludrocortisone acetate, deoxycorticosterone acetate, aldosterone, or the like.

In specific embodiments, the additional therapeutic agent is an immunosuppressant. Immunosuppressants include, by way of non-limiting example, tacrolimus, cyclosporin, rapamicin, methotrexate, cyclophosphamide, azathioprine, mercaptopurine, mycophenolate, and FTY720.

In some embodiments, one or more of the anti-cancer agents are proapoptotic agents. Examples of anti-cancer agents include, by way of non-limiting example: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa—N1; interferon alfa—N3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin—N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor—Saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N—Substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In some embodiments, provided herein is a method of treating lymphoma comprising administering a therapeutically effective amount of a compound described herein in combination with an antibody to CD20 and/or a CHOP (cyclophosphamide, doxorubicin, vincristine, and prednisone) therapy. In certain embodiments, provided herein is a method of treating leukemia comprising administering a therapeutically effective amount of a compound described herein in combination with ATRA, methotrexate, cyclophosphamide and the like.

Pharmaceutical Compositions

In certain embodiments, pharmaceutical compositions are formulated in a conventional manner using one or more physiologically acceptable carriers including, e.g., excipients and auxiliaries which facilitate processing of the active compounds into preparations which are suitable for pharmaceutical use. In certain embodiments, proper formulation is dependent upon the route of administration chosen. A summary of pharmaceutical compositions described herein is found, for example, in *Remington: The Science and Practice of Pharmacy,* Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A pharmaceutical composition, as used herein, refers to a mixture of a compound described herein, such as, for example, a compound of any of Formulas I, Ia, II, IIa, IIb or IIc, with other chemical components, such as carriers, stabilizers, diluents, dispersing agents, suspending agents, thickening agents, and/or excipients. In certain instances, the pharmaceutical composition facilitates administration of the compound to an individual or cell. In certain embodiments of practicing the methods of treatment or use provided herein, therapeutically effective amounts of compounds described herein are administered in a pharmaceutical composition to an individual having a disease, disorder, or condition to be treated. In specific embodiments, the individual is a human. As discussed herein, the compounds described herein are either utilized singly or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

In certain embodiments, a pharmaceutical compositions described herein includes one or more compound described herein, e.g., a compound of any of Formulas I, Ia, II, IIa, IIb or IIc, as an active ingredient in free-acid or free-base form, or in a pharmaceutically acceptable salt form. In some embodiments, the compounds described herein are utilized as an N-oxide or in a crystalline or amorphous form (i.e., a polymorph). In some situations, a compound described herein exists as tautomers. All tautomers are included within the scope of the compounds presented herein. In certain embodiments, a compound described herein exists in an unsolvated or solvated form, wherein solvated forms comprise any pharmaceutically acceptable solvent, e.g., water, ethanol, and the like. The solvated forms of the compounds presented herein are also considered to be disclosed herein.

A "carrier" includes, in some embodiments, a pharmaceutically acceptable excipient and is selected on the basis of compatibility with compounds disclosed herein, such as, compounds of any of Formulas I, Ia, II, IIa, IIb or IIc, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences,* Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Moreover, in certain embodiments, the pharmaceutical compositions described herein is formulated as a dosage form. As such, in some embodiments, provided herein is a dosage form comprising a compound described herein, e.g., a compound of any of Formulas I, Ia, II, IIa, IIb or IIc, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include an additional therapeutic compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in *Remington's Pharmaceutical Sciences,* 20th Edition (2000), a film coating is provided around the formulation of the compound of any of Formula I-V. In one embodiment, a compound described herein is in the form of a particle and some or all of the particles of the compound are coated. In certain embodiments, some or all of the particles of a compound described herein are microencapsulated. In some embodiment, the particles of the compound described herein are not microencapsulated and are uncoated.

Assays

Kinase Inhibition and Binding Assays

Inhibition of various kinases is measured by suitable methods, such as, by way of a non-limiting example, the methods discussed in the Upstate KinaseProfiler Assay Protocols June 2003 publication.

In certain embodiments, provided herein are in vitro assays for identifying compounds that inhibit kinases by
  a. providing a solution of a kinase in a buffer (e.g. phosphate saline buffer);
  b. contacting the kinase solution with a kinase substrate and a phosphate donor (e.g. ATP) and incubating the solution for a suitable length of time to form a phosphorylated substrate;
  c. detecting the phosphorylated substrate by a suitable method (e.g., detection of $\gamma^{32}$P-ATP using a scintillation counter, or the use of detectable secondary antibodies (ELISA))

In certain embodiments, formation of a phosphorylated substrate may be detected using any appropriate technique, such as the detection of ATP concentration (e.g. Kinase-Glo® assay system (Promega). Kinase inhibitors are identified by detecting the formation of a phosphorylated substrate in the presence and/or absence of a test compound (see Examples section below).

In certain embodiments, provided herein are cell-based assays for identifying compounds that inhibit kinases by
  a. providing cells containing a kinase (e.g. JURKAT cells);
  b. contacting the cells with an activating agent (e.g. a growth factor) to activate the kinase;
  c. incubating the cells in the presence of absence of the test compound for a suitable length of time;
  d. lysing the cells and detecting the presence of phosphorylated substrate by an appropriate method (e.g. ELISA).

The detection of a decreased amount of phosphorylated substrate produced in the presence of the test compound relative to the amount produced in the absence of the test compound indicates kinase inhibition. In some instances, cells containing a kinase may be contacted with a radiolabeled substrate and a test compound. The incorporation of the radiolabeled substrate in the cell is detected using a suitable method (e.g. a scintillation counter). The detection of decreased incorporation of the radiolabeled substrate in the cell relative to the amount incorporated in the absence of the test compound indicates kinase inhibition.

The binding of a compound to a kinase is measured using any suitable method, e.g., a test kit manufactured by Discoverx (Fremont, Calif.), ED—Staurosporine NSIP™ Enzyme Binding Assay Kit (see U.S. Pat. No. 5,643,734) may be used. Kinase activity may also be assayed as in U.S. Pat. No. 6,589,950, which is incorporated herein by reference.

Suitable kinase inhibitors may be selected from the compounds of the invention through protein crystallographic screening, as disclosed in, for example Antonysamy, et al., PCT Publication No. WO03087816A1, which is incorporated herein by reference.

Computer modeling techniques are also optionally used to assess the potential modulating or binding effect of a chemical compound on kinases. If computer modeling indicates a strong interaction, the molecule is optionally synthesized and tested for its ability to bind to kinases and/or inhibit or reduce the activity of kinases.

EXAMPLES

Example 1

Synthesis of 1-(3-(4-amino-3-(3-fluoro-4-(pyridin-2-ylmethoxy)phenyl)-1H-pyrazolo[3,4-d]pyrimidin-1-yl)piperidin-1-yl)prop-2-en-1-one

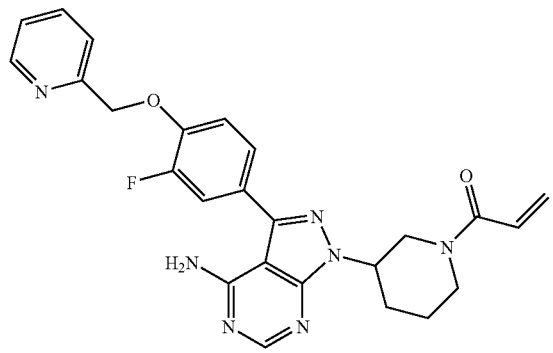 [SMILES: C=CC(=O)N1CCCC(n2nc(-c3ccc(OCc4ccccn4)c(F)c3)c3c(N)ncnc32)C1]

Step 1: Synthesis of 2-((2-fluoro-4-(4,4,5,5-tetramethyl-1,3,2-dioxaborolan-2-yl)phenoxy)methyl)pyridine

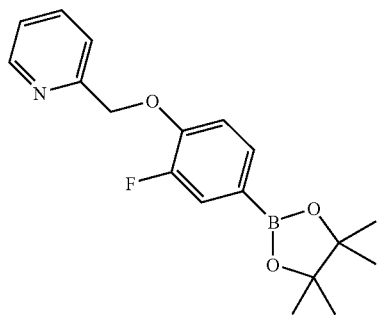 [SMILES: CC1(C)OB(c2ccc(OCc3ccccn3)c(F)c2)OC1(C)C]

2-fluoro-4-(4,4,5,5-tetramethyl-1,3,2-dioxaborolan-2-yl)phenol (1 equivalent), 2-(chloromethyl)pyridine (1.1 equivalent), K₂CO₃ (3 equivalents), and KI (0.1 equivalents) are refluxed in acetone overnight. The mixture is cooled, filtered, the filtrate is concentrated and purified by column chromatography.

Step 2: Synthesis of 3-(3-fluoro-4-(pyridin-2-ylmethoxy)phenyl)-1H-pyrazolo[3,4-d]pyrimidin-4-amine

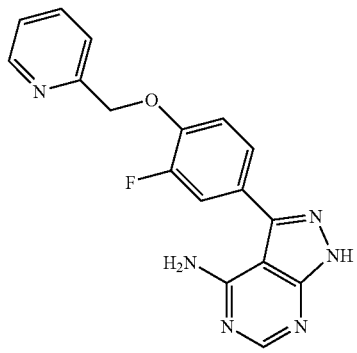 [SMILES: Nc1ncnc2[nH]nc(-c3ccc(OCc4ccccn4)c(F)c3)c12]

1H-pyrazolo[3,4-d]pyrimidin-4-amine (1 equivalent), N-iodosuccinimide (1.25 equivalents) and AIBN (0.1 equivalents) are heated in acetonitrile for 10 h. The reaction is filtered and the filtered material (1 equivalent) is placed in DMF. Pd(dppf)Cl₂ (0.6 equivalents), KI (0.1 equivalents), K₃PO₄ (3 equivalents) and 2-((2-fluoro-4-(4,4,5,5-tetramethyl-1,3,2-dioxaborolan-2-yl)phenoxy)methyl)pyridine (1 equivalent) are added and the mixture is heated at 80° C. overnight. The reaction is partitioned between EtOAc and water, the organic layer is separated, washed with water, brine, dried over Na₂SO₄ and filtered. The filtrate is concentrated under reduced pressure and purified by column chromatography.

Step 3: Synthesis of tert-butyl 3-(4-amino-3-(3-fluoro-4-(pyridin-2-ylmethoxy)phenyl)-1H-pyrazolo[3,4-d]pyrimidin-1-yl)piperiine-1-carboxylate

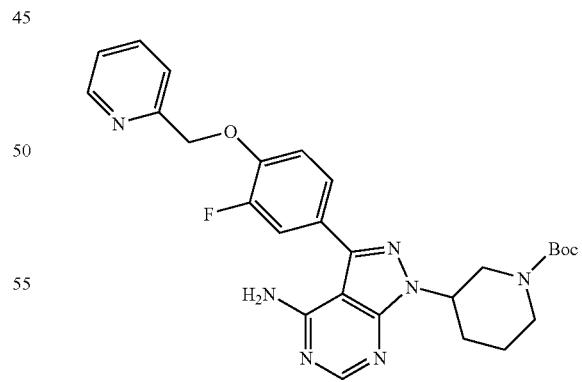

The material from Step 2 (1 equivalent) is placed in THF. Triphenyl phosphine (1.5 equivalents) is added, followed by dropwise addition of DEAD (3 equivalents). Tert-butyl 3-hydroxypiperidine-1-carboxylate (1.2 equivalents) is added and the mixture is stirred at room temperature overnight. The reaction mixture is partitioned between EtOAc and water, the organic layer is separated, washed with water, brine, dried over Na$_2$SO$_4$ and filtered. The filtrate is concentrated under reduced pressure and purified by column chromatography.

Step 4: Synthesis of 1-(3-(4-amino-3-(3-fluoro-4-(pyridin-2-ylmethoxy)phenyl)-1H-pyrazolo[3,4-d]pyrimidin-1-yl)piperidin-1-yl)prop-2-en-1-one The material from Step 3 (1 equivalent) is placed in CH$_2$Cl$_2$. TFA (excess, 10 equivalents) is added to the reaction mixture. The reaction is stirred at room temperature for 2 h. The solvents are removed in vacuo and the residue is dissolved in CH$_2$Cl$_2$. Acryloyl chloride (1.5 equivalents) is added to the reaction mixture followed by addition of Et$_3$N (3 equivalents). The mixture is stirred at room temperature for 6 h and the reaction mixture is partitioned between CH$_2$Cl$_2$ and water, the organic layer is separated, washed with water, brine, dried over MgSO$_4$ and filtered. The filtrate is concentrated under reduced pressure and purified by column chromatography.

The compounds set forth in FIGS. 1 and 2 are synthesized according to a similar procedure as described in Example 1 using the appropriate starting materials and reagents.

Example 2

Synthesis of (E)-5-(3—CHloro-4-(3-fluorobenzyloxy)phenyl)-7-(3-(2-(phenylsulfonyl)vinyl)cyclohexyl)-7H-pyrrolo[2,3-d]pyrimidin-4-amine

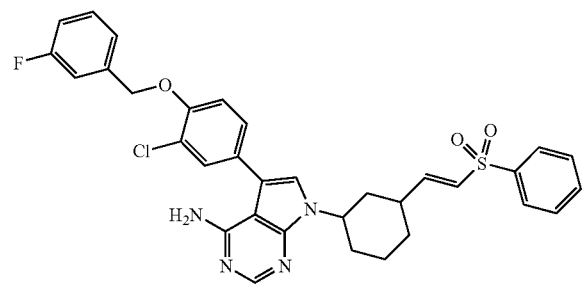 [SMILES: Nc1ncnc2c1c(-c1ccc(OCc3cccc(F)c3)c(Cl)c1)cn2C1CCCC(/C=C/S(=O)(=O)c2ccccc2)C1]

Step 1: Synthesis of 3-(4-amino-5-(3—CHloro-4-(3-fluorobenzyloxy)phenyl)-7H-pyrrolo[2,3-d]pyrimidin-7-yl)cyclohexanecarbaldehyde

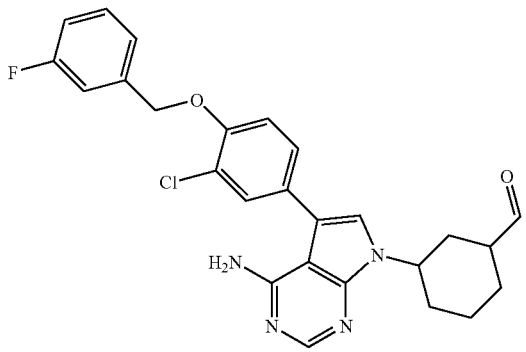 [SMILES: Nc1ncnc2c1c(-c1ccc(OCc3cccc(F)c3)c(Cl)c1)cn2C1CCCC(C=O)C1]

5-(3—CHloro-4-(3-fluorobenzyloxy)phenyl)-7H-pyrrolo[2,3-d]pyrimidin-4-amine (prepared according to a similar procedure as described in Example 1) (1 equivalent) is placed in THF. Triphenyl phosphine (1.5 equivalents) is added, followed by dropwise addition of DEAD (3 equivalents). 3-(1,3-dioxolan-2-yl)cyclohexanol (1 equivalent) is added and the mixture is stirred at room temperature overnight. The reaction mixture is partitioned between EtOAc and water, the organic layer is separated, washed with water, brine, dried over Na$_2$SO$_4$ and filtered. The filtrate is concentrated under reduced pressure and suspended in acetone. p-Toluensulfonic acid (0.6 equivalent) is added and the mixture is refluxed for 4 h. The mixture is filtered, the filtrate is concentrated in vacuo and purified by column chromatography.

Step 2: Synthesis of (E)-5-(3—CHloro-4-(3-fluorobenzyloxy)phenyl)-7-(3-(2-(phenylsulfonyl)vinyl)cyclohexyl)-7H-pyrrolo[2,3-d]pyrimidin-4-amine Diethyl(methylsulfonylmethyl)phosphonate (MSMP) is prepared according to the procedure described in U.S. Pat. No. 6,287,840. To a solution of MSMP (1 equivalent) is added sodium hydride (60% in mineral oil) (2 equivalents) The mixture is stirred for 15 minutes. The material from Step 1 (1 equivalent) is dissolved in 10 mL THF and added to the reaction mixture and the mixture is stirred for 1 hour. The reaction is quenched with 1N HCl and the mixture partitioned between EtOAc and water. The organic layer is separated, washed with water, brine, dried (MgSO$_4$) and filtered. The filtrate is concentrated and purified by recrystallization.

The compounds of FIG. 3 are synthesized according to a similar procedure as described in Example 2 using the appropriate starting materials and reagents.

Example 3

Graft Rejection/Graft Versus Host Assay

Larynges are transplanted from Lewis-Brown—Norway (RT11/n, F1) donors to Lewis (RT11) recipients. Recipients receive 7 days of treatment with a compound that is modified or substituted with an electrophile subject to nucleophilic substitution or nucleophilic addition with a cysteine residue (e.g., a compound of any of Formulas I, Ia, II, IIa, IIb or IIc) and mouse anti-rat alphabeta T-cell-receptor (TCR) monoclonal antibodies. Histology, mixed lymphocyte reaction (MLR), skin grafting, and flow cytometry assess functional tolerance, efficacy of immunodepletion, and donor-specific chimerism. At 100 days, the survival rate, and allograft tolerance of the mice is determined. Skin grafting, MLR, and flow cytometry are examined to confirm that tolerance is neither donor-specific nor related to systemic immunocompromise.

Example 4

Graft Rejection/Graft Versus Host Assay

Larynges are transplanted from Lewis-Brown-Norway (RT11/n, F1) donors to Lewis (RT11) recipients. Recipients receive 7 days of treatment with compound 12 and mouse anti-rat alphabeta T-cell-receptor (TCR) monoclonal antibodies. Histology, mixed lymphocyte reaction (MLR), skin grafting, and flow cytometry assess functional tolerance, efficacy of immunodepletion, and donor—Specific chimerism. At 100 days, the survival rate, and allograft tolerance of the mice is determined. Skin grafting, MLR, and flow cytometry are examined to confirm that tolerance is neither donor—Specific nor related to systemic immunocompromise.

Example 5

Graft Rejection/Graft Versus Host Assay

Larynges are transplanted from Lewis-Brown-Norway (RT11/n, F1) donors to Lewis (RT11) recipients. Recipients receive 7 days of treatment with compound 24 and mouse anti-rat alphabeta T-cell-receptor (TCR) monoclonal antibodies. Histology, mixed lymphocyte reaction (MLR), skin grafting, and flow cytometry assess functional tolerance, efficacy of immunodepletion, and donor-specific chimerism. At 100 days, the survival rate, and allograft tolerance of the mice is determined. Skin grafting, MLR, and flow cytometry are examined to confirm that tolerance is neither donor—Specific nor related to systemic immunocompromise.

Example 6

Treatment of Breast Cancer

Human Clinical Trial of the Safety and/or Efficacy of compound 12 therapy

Objective: To compare the safety and pharmacokinetics of administered compound 12

Study Design: This will be a Phase I, single-center, open-label, randomized dose escalation study followed by a Phase II study in cancer patients with disease that can be biopsied (e.g., Breast Cancer). Patients should not have had exposure to MS compound 12 prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive oral compound 12 daily for 5 consecutive days or 7 days a week. Doses of compound 12 may be held or modified for toxicity based on assessments as outlined below. Treatment repeats every 28 days in the absence of unacceptable toxicity. Cohorts of 3-6 patients receive escalating doses of compound 12 until the maximum tolerated dose (MTD) for compound 12 is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients who are tamoxifen-refractory and express HER2 receive compound 12 as in phase I at the MTD determined in phase I. Treatment repeats every 6 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of compound 12 Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to compound 12 therapy: Patient response is assessed via imaging with X-ray, PET/CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria or other similar response criteria. (Therasse et al, *J. Natl. Cancer Inst.* 2000 Feb. 2; 92(3):205-16; http://ctep.cancer.gov/forms/TherasseRECISTJN-CI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 10

Treatment of Epithelial Ovarian Adenocarcinoma

Human Clinical Trial of the Safety and/or Efficacy of compound 24 therapy

Objective: To compare the safety and pharmacokinetics of administered compound 24

Study Design: This will be a Phase I, single-center, open-label, randomized dose escalation study followed by a Phase II study in cancer patients with disease that can be biopsied (e.g., ovarian carcinoma). Patients should not have had exposure to MS compound 24 prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive oral compound 24 daily for 5 consecutive days or 7 days a week. Doses of compound 24 may be held or modified for toxicity based on assessments as outlined below. Treatment repeats every 28 days in the absence of unacceptable toxicity. Cohorts of 3-6 patients receive escalating doses of compound 24 until the maximum tolerated dose (MTD) for compound 24 is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive compound 24 as in phase I at the MTD determined in phase I. Treatment repeats every 6 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of compound 24 Venous blood samples (5 mL) for determination of serum concentrations are obtained at about 10 minutes prior to dosing and at approximately the following times after dosing: days 1, 2, 3, 4, 5, 6, 7, and 14. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 2, 3, 4, 5, 6, 7, and 14. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to compound 24 therapy: Patient response is assessed via imaging with X-ray, PET/CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria or other similar response criteria. (Therasse et al, *J. Natl. Cancer Inst.* Feb. 2, 2000; 92(3):205-16; http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 14

Drug Screening Assay

Protein kinase activity results in the incorporation of radio labeled Compound 100 (Control compound) (e.g., tritiated Compound 100) into a peptide or protein substrate. The measurement of the amount of radioactivity incorporated into a substrate as a function of time, kinase (e.g., BTK, BMX, TEC, TXK, ITK, EGFR, ErbB2, ErbB4, JAK3, and/or BLK) concentration, and radiolabeled Compound 100 concentration allows radio labeled Compound 100 activity to be quantified (and utilized as a standard or control). The activity is expressed as a 'unit', where 1 unit corresponds to the amount of protein kinase that catalyzes the incorporation of 1 nanomole of phosphate into the standard substrate in 1 minute. Specific activity is defined as units of activity per milligram protein. Up to 40 samples can be assayed manually at one time, and the assay takes one person less than 1 hour to complete. (See, e.g., *Nature Protocols* 1, 968-971 (2006).)

In one instance, radio labeled Compound 100 is contacted with a select protein kinase (e.g., BTK, BMX, TEC, TXK, ITK, EGFR, ErbB2, ErbB4, JAK3, and/or BLK) in combination with a candidate compound (e.g., an electrophilically enhanced compound, such as one set for in any of Formulas I, Ia, II, IIa, IIb or IIc). The measurement of the amount of radioactivity incorporated into a substrate as a function of time, kinase (e.g., BTK, BMX, TEC, TXK, ITK, EGFR, ErbB2, ErbB4, JAK3, and/or BLK) concentration, radio labeled Compound 100 concentration, and candidate compound concentration allows the activity (e.g., with respect to Compound 100) of the candidate compound to be quantified. In particular, over time, in some instances, a candidate compound that irreversibly binds the kinase, the concentration of the radio labeled Compound 100 bound to the kinase may decrease over time. In other instances, a candidate compound that has significantly greater activity than Compound 100 may provide an assay wherein the radio labeled Compound 100 does not show a significant amount of binding to the kinase at any time.

Alternatively, radio labeled candidate compounds (e.g., tritiated) are optionally utilized and their activities are directly measured.

Example 15

Luminescence-Based Kinase Assay

This assay makes use of an ATP depletion assay (Kinase-Glo®, Promega Corporation, Madison, Wis.) to quantitate kinase activity of a candidate compound (e.g., an electrophilically enhanced compound, such as one set forth in any of Formulas I, Ia, II, IIa, IIb or IIc).

The following stock solutions are prepared: 10 mM solution of Compound 100; 100 mM HEPES buffer, pH 7.5 (5 ml 1M stock+45 ml miliQH$_2$O); 10 mM ATP (5.51 mg/ml in dH$_2$O) (diluted 50 µl into total of 10 ml miliQH$_2$O daily=50 µM ATP working stock); 1% BSA (1 g BSA in 100 ml 0.1 M HEPES, pH 7.5), 100 mM MgCl$_2$; 200 µM Staurosporine, 2×Kinase-Glo® reagent.

Standard Assay Setup for 384-well format (20 µl kinase reaction, 40 µl detection reaction): 10 mM MgCl$_2$, 100 µM Compound 100; 0.1% BSA; 1 µl candidate compound (in DMSO); 0.4 µg/ml kinase domain; 10 µM ATP; 100 mM HEPES buffer. Positive controls contain DMSO with no test compound. Negative controls contain 10 µM staurosporine. The kinase reactions are initiated at time t=0 by the addition of ATP. Kinase reactions are incubated at 21° C. for 30 min, then 20 μl of Kinase-Glo™ reagent is added to each well to quench the kinase reaction and initiate the luminescence reaction. After a 20 min incubation at 21° C., the luminescence is detected in a plate-reading luminometer. The luminescent signal from ATP remaining in solution following the kinase reaction is detected in a plate-reading luminometer. The luminescent signal is inversely correlated with the amount of kinase activity. Activity is optionally compared to the activity of compound 100.

Example 16

Computational Assays

Computational assays are used to identify compounds with a strong interaction (e.g., strongest interaction and/or best fit). Docking programs such as, for example, DOCK, or GOLD, are used to identify compounds that bind to the active site and/or other binding pockets. Compounds are screened against more than one binding pocket of the protein structure, or more than one set of coordinates for the same protein, taking into account different molecular dynamic conformations of the protein. Consensus scoring is used to identify the compounds that are the best fit for the protein (Charifson, P. S. et al., J. Med. Chem. 42: 5100-9 (1999)). Data obtained from more than one protein molecule structure is scored according to the methods described in Klingler et al., U.S. Utility Application, filed May 3, 2002, entitled "Computer Systems and Methods for Virtual Screening of Compounds."

Electrophilic or other binding groups in test compounds are computationally evaluated by means of a series of steps in which chemical groups or fragments are screened and selected for their ability to associate with the individual binding pockets, residues or other areas of kinases. Selected fragments or chemical groups are positioned in a variety of orientations, or docked, within binding pockets of kinases (Blaney, J. M. and Dixon, J. S., Perspectives in Drug Discovery and Design, 1:301, 1993). Manual docking is accomplished using any suitable software, such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., J. Comp. Chem. 4:187-217, 1983), AMBER (Weiner, et al., J. Am. Chem. Soc. 106: 765-84, 1984) and C.sup.2 MMFF (Merck Molecular Force Field; Accelrys, San Diego, Calif.). Other automated docking programs such as DOCK (Kuntz et al., J. Mol. Biol., 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., J. Mol. Biol. 245:43-53, 1995); and FLEXX (Tripos, St. Louis, Mo.; Rarey, M., et al., J. Mol. Biol. 261:470-89, 1996) are used to screen compounds.

Evaluation of compound deformation energy and electrostatic interaction is accomplished using any suitable program such as Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); DelPhi (Accelrys, Inc., San Diego, Calif., ©1995); and AMSOL (University of Minnesota) (Quantum Chemistry Program Exchange, Indiana University).

What is claimed is:
1. A compound of Formula I:

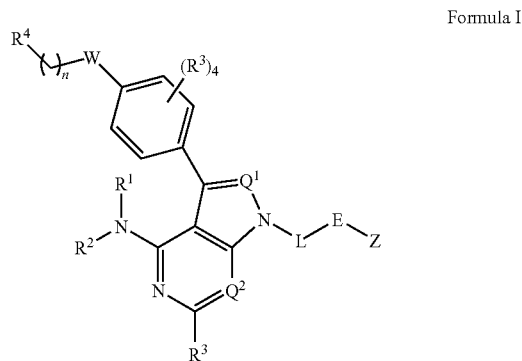

Formula I wherein:
each $R^1$
and $R^2$ is H, substituted or unsubstituted alkyl, substituted or unsubstituted heteroalkyl, $C(=O)R^5$ or $C(=NR^5)$; wherein $R^5$ is H, hydroxy, substituted or unsubstituted alkyl or substituted or unsubstituted alkoxy;
each $R^3$ is independently H, halo, hydroxy, CN, substituted or unsubstituted alkyl, substituted or unsubstituted alkoxy, or substituted or unsubstituted heteroalkyl;
each $R^4$ is independently substituted or unsubstituted heteroalkyl, substituted or unsubstituted aryl, substituted or unsubstituted heteroaryl, substituted or unsubstituted cycloalkyl, or substituted or unsubstituted heterocycloalkyl;
W is $—CH_2—$, $—C≡C—$, O, S, or $NR^1$;
n is 1-7
$Q^1$ is N;
$Q^2$ is N;
L is $A_p$, wherein
each A is independently $NR^1$, $S(O)_q$, O, $C(=X)Y$, $Y(C=X)$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;
p is 0-5;
E is an electrophile selected from:

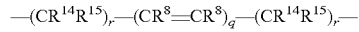

wherein
$R^{14}$ and $R^{15}$ are independently H, CN, $NO_2$, substituted or unsubstituted alkyl, substituted or unsubstituted aryl, or substituted or unsubstituted heteroaryl, or taken together are $=S$, $=N—OR^{11}$, or $=O$; wherein each $R^{11}$ is independently substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;
each $R^8$ is independently H, halo, hydroxy, alkoxy, cyano, nitro, $S(O)_{1-2}R^{11}$, $—C(=X)YR^{11}$, $—YC(=X)R^{11}$, substituted or unsubstituted alkyl, substituted or unsubstituted aryl, substituted or unsubstituted cycloalkyl, substituted or unsubstituted heteroaryl, substituted or unsubstituted heterocycloalkyl, substituted or unsubstituted heteroalkyl, or two $R^8$ are taken together to form a bond;

each r is independently 0-2;

q is 1-2;

Z is $—(Z^1)_k—Z^2$ $Z^1$ is $NR^6$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl $Z^2$ is H, $NR^6{}_2$, $S(O)_q R^6$, $OR^6$, $—C(=X)YR^6$, $—Y(C=X)R^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

each $R^6$ is independently H, halo, hydroxy, alkoxy, cyano, nitro, $—C(=X)YR^7$, $—YC(=X) R^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein $R^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;

k is 0-4;

each X is independently S or O;

each Y is independently S or O;

or a pharmaceutically acceptable salt thereof.

2. The compound of claim 1 wherein E is an electrophile subject to nucleophilic substitution or nucleophilic addition when contacted with a thiol or thiolate.

3. The compound of claim 1, wherein $R^1$ and $R^2$ are independently H or substituted or unsubstituted alkyl.

4. The compound of claim 1, wherein $R^3$ is H, halo, substituted or unsubstituted alkyl, or substituted or unsubstituted alkoxy.

5. The compound of claim 1, wherein W is $—CH_2—$ or O.

6. The compound of claim 1, wherein n is 1-3.

7. The compound of claim 1, wherein E is $—(C=O)—(CH=CH)—$, $—(CH=CH)—(C=O)—$, $—C(CN)=CH—$, $—CH=C(CN)—$, $—C(NO_2)=CH—$, or $—CH=C(NO_2)$.

8. The compound of claim 1, wherein n is 1 or 2, and wherein one A is tetrahydroquinolinyl, quinolinyl, tetrahydroisoquinolinyl, isoquinolinyl, phenyl, cyclohexyl, cyclopentyl, pyridinyl, pyrimidinyl, piperidinyl, homopiperidinyl, pyrrolidinyl, piperazinyl, or morpholino.

9. The compound of claim 1, wherein $Z^2$ is $NR^6{}_2$, substituted or unsubstituted heteroalkyl, substituted or unsubstituted piperidinyl, substituted or unsubstituted pyrrolidinyl, substituted or unsubstituted piperazinyl or a substituted or unsubstituted morpholino.

10. The compound of claim 1, wherein $R^4$ is substituted or unsubstituted aryl, or substituted or unsubstituted heteroaryl.

11. The compound of claim 1 having the Formula II:

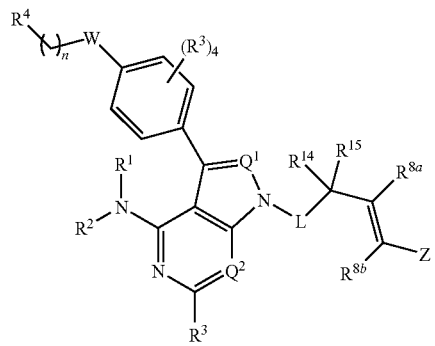

Formula II wherein $R^3$ is H, halo, substituted or unsubstituted alkyl or substituted or unsubstituted alkoxy;

$R^4$ is substituted or unsubstituted aryl, substituted or unsubstituted heteroaryl, substituted or unsubstituted cycloalkyl, or substituted or unsubstituted heterocycloalkyl;

$R^{14}$ is H;

$R^{15}$ is H; or $R^{14}$ and $R^{15}$ taken together are =O;

$R^{8a}$ is H, lower alkyl, CN, $NO_2$, or $SO_2R^{11}$; and $R^{8b}$ is H, CN, $NO_2$, or $SO_2R^{11}$.

12. The compound of claim 11, wherein $R^{14}$ and $R^{15}$ taken together are =O, and wherein $R^{8a}$ and $R^{8b}$ are H.

13. A pharmaceutical composition comprising a therapeutically effective amount of a compound of Formula I:

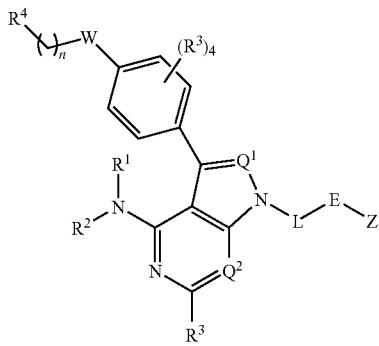

Formula I wherein:

each $R^1$ and $R^2$ is H, substituted or unsubstituted alkyl, substituted or unsubstituted heteroalkyl, $C(=O)R^5$ or $C(=NR^5)$; wherein $R^5$ is H, hydroxy, substituted or unsubstituted alkyl or substituted or unsubstituted alkoxy;

each $R^3$ is independently H, halo, hydroxy, CN, substituted or unsubstituted alkyl, substituted or unsubstituted alkoxy, or substituted or unsubstituted heteroalkyl;

each $R^4$ is independently substituted or unsubstituted heteroalkyl, substituted or unsubstituted aryl, substituted or unsubstituted heteroaryl, substituted or unsubstituted cycloalkyl, or substituted or unsubstituted heterocycloalkyl;

W is —CH$_2$—, —C≡C—, O, S, or NR$^1$;
n is 1-7
Q$^1$ is N;
Q$^2$ is N;
L is A$_p$, wherein
 each A is independently NR$^1$, S(O)$_q$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each q is independently 0-2;
 p is 0-5;
E is an electrophile selected from:

—(CR$^{14}$R$^{15}$)$_r$—(CR$^8$=CR$^8$)$_q$—(CR$^{14}$R$^{15}$)$_r$— wherein
 R$^{14}$ and R$^{15}$ are independently H, CN, NO$_2$, substituted or unsubstituted alkyl, substituted or unsubstituted aryl, or substituted or unsubstituted heteroaryl, or taken together are =S, =N—OR$^{11}$, or =O; wherein each R$^{11}$ is independently substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;
 each R$^8$ is independently H, halo, hydroxy, alkoxy, cyano, nitro, S(O)$_{1-2}$R$^{11}$, —C(=X)YR$^{11}$, —YC(=X)R$^{11}$, substituted or unsubstituted alkyl, substituted or unsubstituted aryl, substituted or unsubstituted cycloalkyl, substituted or unsubstituted heteroaryl, substituted or unsubstituted heterocycloalkyl, substituted or unsubstituted heteroalkyl, or two R$^8$ are taken together to form a bond;
 each r is independently 0-2;
 q is 1-2;
Z is —(Z$^1$)$_k$—Z$^2$
 Z$^1$ is NR$^6$, O, C(=X)Y, Y(C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl
 Z$^2$ is H, NR$^6{}_2$, S(O)$_q$R$^6$, OR$^6$, —C(=X)YR$^6$, —Y(C=X)R$^6$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
 each R$^6$ is independently H, halo, hydroxy, alkoxy, cyano, nitro, —C(=X)YR$^7$, —YC(=X) R$^7$, substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl, wherein R$^7$ is substituted or unsubstituted alkyl, substituted or unsubstituted aryl, substituted or unsubstituted cycloalkyl, substituted or unsubstituted heteroaryl, substituted or unsubstituted heterocycloalkyl, or substituted or unsubstituted heteroalkyl;
 k is 0-4;
 each X is independently S or O;
each Y is independently S or O;
or a pharmaceutically acceptable salt thereof;
and a pharmaceutically acceptable carrier.

* * * * *